(12) United States Patent
Edwards et al.

(10) Patent No.: US 8,466,201 B2
(45) Date of Patent: Jun. 18, 2013

(54) POTASSIUM ION CHANNEL MODULATORS AND USES THEREOF

(75) Inventors: Simon David Edwards, Cambridge (GB); Meriel Ruth Kimberly, Cambridge (GB); Kanesalingam Suthaharan, Cambridge (GB); Nawaz Mohammed Khan, Cambridge (GB); Geoff Lawton, Cambridge (GB)

(73) Assignee: Ramot at Tel-Aviv University ltd., Tel-Aviv (IL)

( * ) Notice: Subject to any disclaimer, the term of this patent is extended or adjusted under 35 U.S.C. 154(b) by 11 days.

(21) Appl. No.: 12/746,524

(22) PCT Filed: Dec. 5, 2008

(86) PCT No.: PCT/GB2008/051158
§ 371 (c)(1),
(2), (4) Date: Nov. 28, 2011

(87) PCT Pub. No.: WO2009/071947
PCT Pub. Date: Jun. 11, 2009

(65) Prior Publication Data
US 2012/0065270 A1    Mar. 15, 2012

(30) Foreign Application Priority Data
Dec. 5, 2007  (GB) .................................. 0723794.4

(51) Int. Cl.
C07C 311/35    (2006.01)
C07C 311/40    (2006.01)
A61K 31/18     (2006.01)

(52) U.S. Cl.
USPC ........................................... 514/603; 564/86

(58) Field of Classification Search
None
See application file for complete search history.

(56) References Cited

U.S. PATENT DOCUMENTS

| | | | |
|---|---|---|---|
| 5,231,135 A | 7/1993 | Machell et al. | |
| 6,004,948 A | 12/1999 | Blaschke et al. | |

FOREIGN PATENT DOCUMENTS

| | | |
|---|---|---|
| DE | 2055962 | 5/1971 |
| EP | 0554543 | 8/1993 |
| GB | 1039116 | 8/1966 |
| GB | 1371378 | 10/1974 |
| WO | WO 00/42003 | 7/2000 |
| WO | WO 01/05393 | 1/2001 |
| WO | WO 2004/035037 | 4/2004 |
| WO | WO 2006/124875 | 11/2006 |
| WO | WO 2008/075353 | 6/2008 |
| WO | WO 2008/149163 | 12/2008 |
| WO | WO 2009/071947 | 6/2009 |

OTHER PUBLICATIONS

International Search Report and the Written Opinion Dated Jan. 22, 2010 From the International Searching Authority Re.: Application No. PCT/GB2008/051158.
Kraska et al. "Synthesis and Properties of Disazo Dyes Derived From 4-Amino-2'-Nirodiphenylamine", Dyes and Pigments, XP002553864, 31(2): 97-109, 1996. p. 99, Compounds (2) X(A-3).
Salvin et al. "Relation of Dye Structure to Properties of Diserse Dyes. II. Diphenylamine Yellows", Proceedings of the American Association of Textile Chemists and Colorists, American Dyestuff Reporter, XP009125327, 48(14): 43-47, Jul. 13, 1959. Database CAPLUS, Chemical Abstracts Service, Database Accession No. 1959:91781.
International Preliminary Report on Patentability Dated Jun. 17, 2010 From the International Bureau of WIPO Re. Application No. PCT/GB2008/051158.

*Primary Examiner* — Sreeni Padmanabhan
*Assistant Examiner* — Irina Neagu

(57) ABSTRACT

Compounds of formula (I) and pharmacologically acceptable salts and pro-drugs wherein:

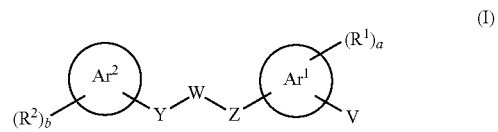

$Ar^1$ and $Ar^2$=aryl or heteroaryl;
a=0 to 5;
$R^1$=alkyl, halogen, haloalkyl, alkoxy, alkoxycarbonyl, carboxyl, hydroxyl, amino, monalkylamino, dialkylamino, nitro, acylamino, alkoxycarbonylamino, alkylsulphonyl, alkylsulphonylamino and cyano and, where a is >1, each $R^1$ is the same or different;
b=0 to 5;
$R^2$=alkyl, halogen, haloalkyl, alkoxy, alkoxycarbonyl, carboxyl, hydroxyl, amino, monalkylamino, dialkylamino, nitro, acylamino, alkoxycarbonylamino, alkylsulphonyl, alkylsulphonylamino and cyano and where b is >1, each $R^2$ is the same or different;

$V=(CR^{3a}R^{3b})_pSO_2N(R^{3b})X$ and $(CR^{3a}R^{3b})_pN(R^{3b})SO_2(X)$;

$W=NR^{4a}$, O, S, S=O, $SO_2$ and $C(R^{4a}R^{4b})_2$;

X=hydroxyalkyl, alkoxyalkyl, haloalkoxyalkyl, aryloxyalkyl, polyalkylene glycol residues, aminoalkyl, monoalkylaminoalkyl, dialkylaminoalkyl and alkyl groups substituted with $\geq 1$ NR8R9 groups wherein R8 and R9+nitrogen atom form a saturated or partially unsaturated heterocyclic group which is optionally further substituted by $\geq 1$ substituents selected from alkyl, halogen, haloalkyl, alkoxy, alkoxycarbonyl, carboxyl, nitro, amino, monoalkylamino, dialkylamino and hydroxyl;
Y and Z each $=(CR^{5a}R^{5b})_{n1}$, C=O, $SO_2$, $C(=O)NR^{5a}$, $C(=O)NR^{5a}SO_2$ or $C=O(R^{5a}R^{5b})_{n2}$;
$R^{3a}$, $R^{3b}$, $R^{4a}$, $R^{4b}$, $R^{5a}$ and $R^{5b}$ each=hydrogen, alkyl, cycloalkyl, aryl or heteroaryl;
n1 and n2 each=0 to 2; and
p=0 to 2;
are excellent selective modulators of potassium ion flux through KCNQ2, KCNQ3 and/or KCNQ2/3 channels, making them of use in treating and preventing a number of conditions including pain and lower urinary tract disorders.

16 Claims, No Drawings

POTASSIUM ION CHANNEL MODULATORS AND USES THEREOF

RELATED APPLICATIONS

This application is a National Phase of PCT Patent Application No. PCT/GB2008/051158 having International filing date of Dec. 5, 2008, which claims the benefit of U.K. Patent Application No. 0723794.4 filed on Dec. 5, 2007. The contents of the above Applications are all incorporated herein by reference.

FIELD OF THE INVENTION

The present invention relates to ion channel modulators, and more particularly to heterocyclic compounds that modulate (preferably open) KCNQ2 (Kv7.2), KCNQ3 (Kv 7.3) and KCNQ2/3 voltage-dependent potassium channels.

BACKGROUND TO THE INVENTION

Voltage-dependent potassium (Kv) channels conduct potassium ions ($K^+$) across cell membranes in response to changes in the membrane voltage and thereby can regulate cellular excitability by modulating (increasing or decreasing) the electrical activity of the cell.

Functional Kv channels exist as multimeric structures formed by the association of four alpha and four beta subunits. The alpha subunits comprise six transmembrane domains, a pore-forming loop and a voltage-sensor and are arranged symmetrically around a central pore. The beta or auxiliary subunits interact with the alpha subunits and can modify the properties of the channel complex to include, but not be limited to, alterations in the channel's electrophysiological or biophysical properties, expression levels or expression patterns.

Functional Kv channels can exist as multimeric structures formed by the association of either identical or dissimilar Kv alpha and/or Kv beta subunits.

Nine Kv channel alpha subunit families have been identified and are termed Kv1-Kv9. As such, there is an enormous diversity in Kv channel function that arises as a consequence of the multiplicity of sub-families, the formation of both homomeric and heteromeric subunits within sub-families and the additional effects of association with beta subunits (M. J. Christie, Clinical and Experimental Pharmacology and Physiology, 1995, 22 (12), 944-951).

The Kv7 channel family consists of at least five members which include one or more of the following mammalian channels: Kv7.1, Kv7.2, Kv7.3, Kv 7.4, Kv7.5 and any mammalian or non-mammalian equivalent or variant (including splice variants) thereof. Alternatively, the members of this family are termed KCNQ1, KCNQ2, KCNQ3, KCNQ4 and KCNQ5 respectively (Dalby-Brown. W et al., Current Topics in Medicinal Chemistry, 2006, 6, 999-1023).

The five members of this family differ in their expression patterns. The expression of Kv 7.1 is restricted to the heart, peripheral epithelial and smooth muscle, whereas the expression of Kv 7.2-Kv 7.4 is limited to the nervous system to include the hippocampus, cortical neurons and dorsal root ganglion neurons (for a review see Delmas. P & Brown. D, Nature, 2005, 6, 850-862).

The neuronal Kv7 channels have been demonstrated to play key roles in controlling neuronal excitation. Kv7 channels, in particular Kv 7.2/Kv 7.3 heterodimers, underlie the M-current, aslowly activating, non-inactivating potassium current found in a number of neuronal cell types. The current has a characteristic time- and voltage-dependence that results in stabilisation of the membrane potential in response to multiple excitatory stimuli. In this way, the M-current is central to controlling neuronal excitability (for a review see Delmas. P & Brown.D, Nature, 2005, 6, 850-862).

The Kv7 channels are also clinically valuable targets, since mutations in the genes of four out of the five members gives rise to a number of human disorders. For example, mutations in the genes for KCNQ2 or KCNQ3 result in a form of juvenile epilepsy called benign familial neonatal convulsions (BNFC) (Jentsch, T. J., Nature Reviews Neuroscience, 2000, 1 (1), 21-30).

Thus, given the key physiological role of Kv7 channels in the nervous system and the involvement of these channels in a number of diseases, the development of modulators of Kv7 channels is very desirable.

Modulators of KCNQ2, KCNQ3 or KCNQ2/3 have potential utility in the treatment, prevention, inhibition, amelioration or alleviation of symptoms of a number of conditions or disease states including:

"Lower Urinary Tract Disorders", this encompasses both painful (any lower urinary tract disorder involving sensations or symptoms that a patient subjectively describes as producing or resulting in pain) and non-painful lower urinary tract disorders (any lower urinary tract disorder involving sensations or symptoms, including mild or general discomfort, that is subjectively described as not producing or resulting in pain). "Lower urinary tract disorders" also includes any lower urinary tract disorder characterised by overactive bladder with and/or without loss of urine, urinary frequency, urinary urgency, and nocturia. Thus, lower urinary tract disorders includes overactive bladder or overactive urinary bladder (including, overactive detrusor, detrusor instability, detrusor hyperreflexia, sensory urgency and the symptoms of detrusor overactivity), urge incontinence or urinary urge incontinence, stress incontinence or urinary stress incontinence, lower urinary tract symptoms including obstructive urinary symptoms such as slow urination, dribbling at the end of urination, inability to urinate and/or the need to strain to urinate at an acceptable rate or irritating symptoms such as frequency and/or urgency. Lower urinary tract disorders may also include neurogenic bladder that occurs as the result of neurological damage due to disorders including but not limited to stroke, Parkinson's disease, diabetes, multiple sclerosis, peripheral neuropathy, or spinal cord lesions. Lower urinary tract disorders may also include prostatitis, interstitial cystitis, benign prostatic hyperplasia, and, in spinal cord injured patients, spastic bladder.

"Anxiety and Anxiety-Related Conditions", this includes, but is not limited to, anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias. Specific anxiety related phobias include, but are not limited to, fear of animals, insects, storms, driving, flying, heights or crossing bridges, closed or narrow spaces, water; blood or injury, as well as extreme fear of inoculations or other invasive medical or dental procedures.

"Epilepsy", includes, but is not limited to, one or more of the following seizures: simple partial seizures, complex partial seizures, secondary generalised seizures, generalised seizures including absence seizures, myoclonic seizures, clonic seizures, tonic seizures, tonic clonic seizures and atonic seizures.

"Pain Disorders", includes but is not limited to one or more on the following: acute pain such as musculoskeletal pain, post-operative pain and surgical pain; chronic pain such as chronic inflammatory pain (e.g. rheumatoid arthritis and osteoarthritis), neuropathic pain (e.g. post-herpetic neuralgia, trigeminal neuralgia and sympathetically-maintained pain) and pain associated with cancer and fibromyalgia; pain associated with migraine; pain (both chronic and acute), and/or fever and/or inflammation of conditions such as rheumatic fever; symptoms associated with influenza or other viral infections, such as the common cold; lower back and neck pain; headache; toothache; sprains and strains; myositis; neuralgia; synovitis; arthritis, including rheumatoid arthritis; degenerative joint diseases, including osteoarthritis; gout and ankylosing spondylitis; tendinitis; bursitis; skin-related conditions, such as psoriasis, eczema, burns and dermatitis; injuries, such as sports injuries and those arising from surgical and dental procedures.

"Gynaecological Pain", for example, dysmenorrhoea, labour pain and pain associated with endometriosis.

"Cardiac Arrhythmias", include, but are not limited to, atrial fibrillation, atrial flutter, atrial arrhythmia and supaventricular tachycardia.

"Thromboembolic Events" such as stroke.

"Cardiovascular Diseases" such as angina pectoris, hypertension and congestive heart failure.

"Disorders of the Auditory System" such as tinnitus.

"Migraine"

"Inflammatory and Immunological Diseases" (or a disorder involving immunosuppression) including inflammatory bowel disease, rheumatoid arthritis, graft rejection, asthma, chronic obstructive pulmonary disease, multiple sclerosis, cystic fibrosis and atherosclerosis.

"Gastrointestinal Disorders" including reflux oesophagitis, functional dyspepsia, motility disorders (including constipation and diarrhoea), and irritable bowel syndrome.

"Vascular and Visceral Smooth Muscle Disorders" including asthma, pulmonary hypertension, chronic obstructive pulmonary disease, adult respiratory distress syndrome, peripheral vascular disease (including intermittent claudication), venous insufficiency, impotence, cerebral and coronary spasm and Raynaud's disease.

"Cell Proliferative Disorders" including restenosis and cancer (including leukemia); treating or preventing gliomas including those of lower and higher malignancy.

"Metabolic Disorders" such as diabetes (including diabetic retinopathy, diabetic nephropathy and diabetic neuropathy), insulin resistance/insensitivity and obesity.

"Memory Loss" including Alzheimer's disease and dementia.

Other "CNS-Mediated Motor Dysfunction Disorders" including Parkinson's disease and ataxia.

"Ophthalmic Disorders" such as ocular hypertension.

Retigabine is an anti-epileptic drug whose mechanism of action involves potassium channel opening activity in neuronal cells (first described in European Patent No. 0554543). Retigabine enhances potassium currents through specific activation of KCNQ2/3 channels (Wickenden, A. D., Molecular Pharmacology, 2000, 58, 591-600). However, retigabine has been reported to have multiple effects in neuronal cells. These include sodium and calcium channel blocking activity (Rundfeldt, C, 1995, Naunyn-Schmiederberg's Arch Pharmacol, 351 (Suppl): R160) and effects on GABA (γ-aminobutyric acid) synthesis and transmission in rat neurons (Kapetanovic, I. M., 1995, Epilepsy Research, 22, 167-173, Rundfeldt, C, 1995, Naunyn-Schmiederberg's Arch Pharmacol, 351 (Suppl):R160).

Thus, in order to overcome unwanted side effects, more selective Kv7 channel modulators are required.

WO04035037 discloses the use of N-phenylanthranilic acid derivatives as modulators of KCNQ2, KCNQ3 and KCNQ2/3 channels. These derivatives have substituents comprising hydroxyalkyl or polyalkylene glycol moieties that are linked to one of the phenyl groups of the N-phenylanthranilic acid moiety via a variety of linkers. There is no disclosure of any compounds having a sulphonamide linker group.

It would be desirable to identify more selective Kv7 channel modulators for the prophylaxis or treatment of a number of disease states including lower urinary tract disorders, inflammatory and immunological diseases and pain indications. Using potassium ion channel patch clamp assays on KCNQ2, KCNQ3 and KCNQ2/3 channels recombinatly expressed in cells lines, a new family of N-phenylanthranilic acid compounds has been found that are excellent selective modulators of potassium ion flux through KCNQ2, KCNQ3 and/or KCNQ2/3 channels.

DESCRIPTION OF THE INVENTION

In a first aspect of the present invention, there is provided a compound of formula (I) or a pharmacologically acceptable salt or pro-drug thereof wherein:

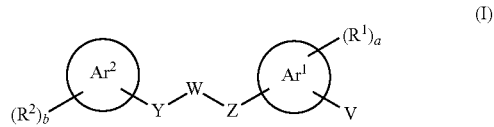

$Ar^1$ and $Ar^2$ are the same or different and each is an aryl group or a heteroaryl group;

a is an integer of from 0 to 5;

$R^1$ is selected from the group consisting of alkyl groups, halogen atoms, haloalkyl groups, alkoxy groups, alkoxycarbonyl groups, carboxyl groups, hydroxyl groups, amino groups, monalkylamino groups, dialkylamino groups, nitro groups, acylamino groups, alkoxycarbonylamino groups, alkylsulphonyl groups, alkylsulphonylamino groups and cyano groups and, where a is greater than 1, each substituent $R^1$ may be the same or different;

b is an integer of from 0 to 5;

$R^2$ is selected from the group consisting of alkyl groups, halogen atoms, haloalkyl groups, alkoxy groups, alkoxycarbonyl groups, carboxyl groups, hydroxyl groups, amino groups, monalkylamino groups, dialkylamino groups, nitro groups, acylamino groups, alkoxycarbonylamino groups, alkylsulphonyl groups, alkylsulphonylamino groups and cyano groups and where b is greater than 1, each substituent $R^2$ may be the same or different;

V is selected from the group consisting of $(CR^{3a}R^{3b})_p$ $SO_2N(R^{3b})X$ and $(CR^{3a}R^{3b})_pN(R^{3b})So_2(X)$;

W is selected from the group consisting of $NR^{4a}$, O, S, S=O, $SO_2$ and $C(R^{4a}R^{4b})_2$;

X is a substituent selected from the group consisting of hydroxyalkyl groups, alkoxyalkyl groups, haloalkoxyalkyl groups, aryloxyalkyl groups, polyalkylene glycol residues, aminoalkyl groups, monoalkylaminoalkyl groups, dialkylaminoalkyl groups and alkyl groups that are substituted with one or more groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms (said saturated or partially unsaturated heterocyclic group optionally further being substituted by one or more substituents selected from the group consisting of alkyl groups, halogen atoms, haloalkyl groups, alkoxy groups, alkoxycarbonyl groups, carboxyl groups, nitro groups, amino groups, monoalkylamino groups, dialkylamino groups and hydroxyl groups);

Y and Z are the same or different and each is a substituent selected from the group consisting of $(CR^{5a}R^{5b})_{n1}$, $C=O$, $SO_2$, $C(=O)NR^{5a}$, $C(=O)NR^{5a}SO_2$ and $C=O(R^{5a}R^{5b})_{n2}$;

$R^{3a}$, $R^{3b}$, $R^{4a}$, $R^{4b}$, $R^{5a}$ and $R^{5b}$ are the same or different and each is selected from the group consisting of hydrogen atoms, alkyl groups, cycloalkyl groups, aryl groups and heteroaryl groups;

n1 and n2 are the same or different and each is an integer of from 0 to 2; and p is an integer of from 0 to 2.

Preferred compounds of the present invention include:

(2) compounds according to (1) and pharmacologically acceptable salts and pro-drugs thereof, wherein $Ar^1$ and $Ar^2$ are the same or different and each is an aryl group having from 5 to 14 carbon atoms or a 5- to 7-membered aromatic heterocyclic group containing from 1 to 3 sulfur atoms, oxygen atoms and/or nitrogen atoms;

(3) compounds according to (1) and pharmacologically acceptable salts and pro-drugs thereof, wherein $Ar^1$ and $Ar^2$ are the same or different and each is an aryl group having from 6 to 10 carbon atoms or a 5- or 6-membered aromatic heterocyclic group containing 1 or 2 sulfur atoms, oxygen atoms and/or nitrogen atoms;

(4) compounds according to (1) and pharmacologically acceptable salts and pro-drugs thereof, wherein $Ar^1$ and $Ar^2$ are the same or different and each is selected from phenyl, pyridyl, furyl, thienyl and pyrrolyl groups;

(5) compounds according to (1) and pharmacologically acceptable salts and pro-drugs thereof, wherein $Ar^1$ and $Ar^2$ are each phenyl;

(6) compounds according to any one of (1) to (5) and pharmacologically acceptable salts and pro-drugs thereof, wherein a is an integer of from 0 to 3;

(7) compounds according to any one of (1) to (5) and pharmacologically acceptable salts and pro-drugs thereof, wherein a is 0 or 1;

(8) compounds according to any one of (1) to (7) and pharmacologically acceptable salts and pro-drugs thereof, wherein $R^1$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where a is greater than 1, each substituent $R^1$ may be the same or different;

(9) compounds according to any one of (1) to (7) and pharmacologically acceptable salts and pro-drugs thereof, wherein $R^1$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent $R^1$ may be the same or different;

(10) compounds according to any one of (1) to (9) and pharmacologically acceptable salts and pro-drugs thereof, wherein b is an integer of from 0 to 4;

(11) compounds according to any one of (1) to (9) and pharmacologically acceptable salts and pro-drugs thereof, wherein b is an integer of from 0 to 3;

(12) compounds according to any one of (1) to (11) and pharmacologically acceptable salts and pro-drugs thereof, wherein $R^2$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where b is greater than 1, each substituent $R^2$ may be the same or different;

(13) compounds according to any one of (1) to (11) and pharmacologically acceptable salts and pro-drugs thereof, wherein $R^2$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where b is greater than 1, each substituent $R^2$ may be the same or different;

(14) compounds according to any one of (1) to (11) and pharmacologically acceptable salts and pro-drugs thereof, wherein $R^2$ is selected from the group consisting of alkyl groups having from 1 to 3 carbon atoms, halogen atoms, haloalkyl groups having from 1 to 3 carbon atoms, alkoxy groups having from 1 to 3 carbon atoms, carboxyl groups, amino groups, hydroxyl groups and cyano groups;

(15) compounds according to any one of (1) to (14) and pharmacologically acceptable salts and pro-drugs thereof, wherein W is selected from the group consisting of $NR^{4a}$, O, S, $S=O$, $SO_2$ and $C(R^{4a}R^{4b})_2$, wherein $R^{4a}$ and $R^{4b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms;

(16) compounds according to any one of (1) to (14) and pharmacologically acceptable salts and pro-drugs thereof, wherein W is selected from the group consisting of $NR^{4a}$, O and S, wherein $R^{4a}$ is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms;

(17) compounds according to any one of (1) to (14) and pharmacologically acceptable salts and pro-drugs thereof, wherein W is a group of formula $NR^{4a}$, wherein $R^{4a}$ is selected from the group consisting of hydrogen atoms, alkyl groups having from 1 to 3 carbon atoms and phenyl groups;

(18) compounds according to any one of (1) to (17) and pharmacologically acceptable salts and pro-drugs thereof, wherein Y and Z are the same or different and each is a substituent selected from the group consisting of $(CR^{5a}R^{5b})_{n1}$, C=O, $SO_2$, C(=O)$NR^{5a}$, C(=O)$NR^{5a}SO_2$ and C=O($R^{5a}R^{5b})_{n2}$, wherein n1 and n2 are the same or different and each is 0 or 1 and $R^{5a}$ and $R^{5b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms;

(19) compounds according to any one of (1) to (17) and pharmacologically acceptable salts and pro-drugs thereof, wherein Y and Z are the same or different and each is a substituent selected from the group consisting of $(CR^{5a}R^{5b})_{n1}$, C=O and C=O($R^{5a}R^{5b})_{n2}$, wherein n1 and n2 are the same or different and each is 0 or 1 and $R^{5a}$ and $R^{5b}$ are the same or different and each is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms;

(20) compounds according to any one of (1) to (17) and pharmacologically acceptable salts and pro-drugs thereof, wherein Y and Z are each a group of formula $(CR^{5a}R^{5b})_{n1}$ wherein each n1 is 0;

(21) compounds according to any one of (1) to (20) and pharmacologically acceptable salts and pro-drugs thereof, wherein V is selected from the group consisting of $(CR^{3a}R^{3b})_pSO_2N(R^{3b})X$ and $(CR^{3a}R^{3b})_pN(R^{3b})SO_2X$, wherein V is selected from the group consisting of $(CR^{3a}R^{3b})_pSO_2N(R^{3b})X$ and $(CR^{3a}R^{3b})_pN(R^{3b})SO_2X$, wherein p is an integer of from 0 to 2, $R^{3a}$ and $R^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms, and X is a substituent selected from the group consisting of hydroxyalkyl groups having from 1 to 6 carbon atoms, polyalkylene glycol residues of general formula HO—[$(CR^{6a}R^{6b})_{c2}]_{c3}$— wherein c1 and c2 are the same or different and each is an integer of from 0 to 4, c3 is an integer of from 1 to 20 and $R^{6a}$, $R^{6b}$, $R^{6c}$ and $R^{6d}$ may be the same or different from each other and each is a hydrogen atom or an alkyl group having from 1 to 6 carbon atoms, aminoalkyl groups having from 1 to 6 carbon atoms, monalkylaminoalkyl groups comprising an aminoalkyl group having from 1 to 6 carbon atoms that is substituted on the nitrogen atom with an alkyl group having from 1 to 6 carbon atoms and a dialkylaminoalkyl groups comprising an aminoalkyl group having from 1 to 6 carbon atoms that is substituted on the nitrogen atom with two alkyl groups that may be the same or different and each is an alkyl group having from 1 to 6 carbon atoms;

(22) compounds according to any one of (1) to (20) and pharmacologically acceptable salts and pro-drugs thereof, wherein V is selected from the group consisting of $(CR^{3a}R^{3b})_pSO_2N(R^{3b})X$ and $(CR^{3a}R^{3b})_pN(R^{3b})SO_2X$, wherein p is an integer of from 0 to 2, $R^{3a}$ and $R^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms which may optionally be substituted with at least one substituent selected from alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups and cyano groups, and 5- to 7-membered aromatic heterocyclic groups containing from 1 to 3 sulfur atoms, oxygen atoms and/or nitrogen atoms, and X is a substituent selected from the group consisting of hydroxyalkyl groups having from 1 to 6 carbon atoms, alkoxyalkyl groups comprising alkyl groups having from 1 to 6 carbon atoms which are substituted with alkoxy groups having from 1 to 6 carbon atoms, haloalkoxyalkyl groups comprising alkyl groups having from 1 to 6 carbon atoms which are substituted with haloalkoxy groups having from 1 to 6 carbon atoms, aryloxyalkyl groups comprising alkyl groups having from 1 to 6 carbon atoms which are substituted with aryloxy groups having from 5 to 14 carbon atoms which may optionally be substituted with at least one substituent selected from alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups and cyano groups, polyalkylene glycol residues of general formula HO—[$(CR^{6a}R^{6b})_{c1}$—O—$(CR^{6c}R^{6d})_{c2}]_{c3}$— wherein c1 and c2 are the same or different and each is an integer of from 0 to 4, c3 is an integer of from 1 to 20 and $R^{6a}$, $R^{6b}$, $R^{6c}$ and $R^{6d}$ may be the same or different from each other and each is a hydrogen atom or an alkyl group having from 1 to 6 carbon atoms, aminoalkyl groups having from 1 to 6 carbon atoms, monalkylaminoalkyl groups comprising an aminoalkyl group having from 1 to 6 carbon atoms that is substituted on the nitrogen atom with an alkyl group having from 1 to 6 carbon atoms and a dialkylaminoalkyl groups comprising an aminoalkyl group having from 1 to 6 carbon atoms that is substituted on the nitrogen atom with two alkyl groups that may be the same or different and each is an alkyl group having from 1 to 6 carbon atoms, and alkyl groups having from 1 to 6 carbon atoms that are substituted with one or more groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms (said saturated or partially unsaturated heterocyclic group optionally further being substituted by one or more substituents selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups having from 2 to 7 carbon atoms, carboxyl groups, carbonyl groups, nitro groups, amino groups, monoalkylamino groups wherein the alkyl group has from 1 to 6 carbon atoms, dialkylamino groups wherein each alkyl group is the same or different and has from 1 to 6 carbon atoms and hydroxyl groups);

(23) compounds according to any one of (1) to (20) and pharmacologically acceptable salts and pro-drugs thereof, wherein V is selected from the group consisting of $(CR^{3a}R^{3b})_pSO_2N(R^{3b})X$ and $(CR^{3a}R^{3b})_pN(R^{3b})SO_2X$, wherein p is an integer of from 0 to 2, $R^{3a}$ and $R^{3b}$ are the same or different and each is selected from the group consisting of hydrogen atoms, alkyl groups having from 1 to 4 carbon atoms, cycloalkyl groups having from 4 to 6 carbon atoms, aryl groups having from 6 to 10 carbon atoms which may optionally be substituted with at least one substituent selected from alkyl groups having from 1 to 4 carbon atoms, halogen atoms, haloalkyl groups having from 1 to 4 carbon atoms, alkoxy groups having from 1 to 4 carbon atoms, alkoxycarbonyl groups wherein the alkoxy group has from 1 to 4 carbon atoms, carboxyl groups, hydroxyl groups and cyano groups, and 5- to 7-membered aromatic heterocyclic groups containing from 1 to 3 sulfur atoms, oxygen atoms and/or nitrogen atoms, and X is a substituent selected from the group consisting of hydroxyalkyl groups having from 1 to 4 carbon atoms, alkoxyalkyl groups comprising alkyl groups having from 1 to 4 carbon atoms which are substituted with alkoxy groups having from 1 to 4 carbon atoms, haloalkoxyalkyl groups comprising alkyl groups having from 1 to 4 carbon atoms which are substituted with haloalkoxy groups having from 1 to 4 carbon atoms, aryloxyalkyl groups comprising alkyl groups having from 1 to 4 carbon atoms which are substituted with aryloxy groups having from 6 to 10 carbon atoms which may optionally be substituted with at least one substituent selected from alkyl groups having from 1 to 4 carbon atoms, halogen atoms, haloalkyl groups having from 1 to 4 carbon atoms, alkoxy groups having from 1 to 4 carbon atoms, alkoxycarbonyl groups wherein the alkoxy group has from 1 to 4 carbon atoms, carboxyl groups, hydroxyl groups and cyano groups, polyalkylene glycol residues of general formula HO—$[(CR^{6a}R^{6b})_{c1}$—O—$(CR^{6c}R^{6d})_{c2}]_{c3}$— wherein c1 and c2 are the same or different and each is an integer of from 1 to 3, c3 is an integer of from 1 to 10 and $R^{6a}$, $R^{6b}$, $R^{6c}$ and $R^{6d}$ may be the same or different from each other and each is a hydrogen atom or an alkyl group having from 1 to 4 carbon atoms, aminoalkyl groups having from 1 to 4 carbon atoms, monalkylaminoalkyl groups comprising an aminoalkyl group having from 1 to 4 carbon atoms that is substituted on the nitrogen atom with an alkyl group having from 1 to 4 carbon atoms and a dialkylaminoalkyl groups comprising an aminoalkyl group having from 1 to 4 carbon atoms that is substituted on the nitrogen atom with two alkyl groups that may be the same or different and each is an alkyl group having from 1 to 4 carbon atoms, and alkyl groups having from 1 to 4 carbon atoms that are substituted with one or more groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms (said saturated or partially unsaturated heterocyclic group optionally further being substituted by one or more substituents selected from the group consisting of alkyl groups having from 1 to 4 carbon atoms, halogen atoms, haloalkyl groups having from 1 to 4 carbon atoms, alkoxy groups having from 1 to 4 carbon atoms, alkoxycarbonyl groups having from 2 to 5 carbon atoms, carboxyl groups, carbonyl groups, nitro groups, amino groups, monoalkylamino groups wherein the alkyl group has from 1 to 4 carbon atoms, dialkylamino groups wherein each alkyl group is the same or different and has from 1 to 4 carbon atoms and hydroxyl groups);

(24) compounds according to any one of (1) to (20) and pharmacologically acceptable salts and pro-drugs thereof, wherein V is a group of formula of $(CR^{3a}R^{3b})_pSO_2N(R^{3b})X$, wherein p is an integer of 0 or 1, $R^{3a}$ and $R^{3b}$ are the same or different and each is selected from the group consisting of hydrogen atoms and alkyl groups having from 1 to 4 carbon atoms, and X is a substituent selected from the group consisting of hydroxyalkyl groups having from 1 to 4 carbon atoms and polyalkylene glycol residues of general formula HO—$[(CR^{6a}R^{6b})_{c1}$—O—$(CR^{6c}R^{6d})_{c2}]_{c3}$— wherein c1 and c2 are the same or different and each is an integer of from 1 to 3, c3 is an integer of from 1 to 10 and $R^{6a}$, $R^{6b}$, $R^{6c}$ and $R^{6d}$ may be the same or different and each is a hydrogen atom or an alkyl group having from 1 to 4 carbon atoms;

(25) compounds according to any one of (1) to (21) and pharmacologically acceptable salts and pro-drugs thereof, wherein V is a group of formula of $(CR^{3a}R^{3b})_pSO_2N(R^{3b})X$, wherein p is an integer of 0 or 1, each of $R^{3a}$ and $R^{3b}$ is a hydrogen atom, and X is a hydroxylalkyl group having from 1 to 4 carbon atoms or a polyalkylene glycol residue of general formula HO—$[(CR^{6a}R^{6b})_{c1}$—O—$(CR^{6c}R^{6d})_{c2}]_{c3}$— wherein c1 and c2 are the same or different and each is 1 or 2, c3 is an integer of from 1 to 6 and each of $R^{6a}$, $R^{6b}$, $R^{6c}$ and $R^{6d}$ is a hydrogen atom;

(26) a compound according to (1) or a pharmacologically acceptable salt or pro-drug thereof, wherein:

$Ar^1$ and $Ar^2$ are the same or different and each is an aryl group having from 5 to 14 carbon atoms or a 5- to 7-membered aromatic heterocyclic group containing from 1 to 3 sulfur atoms, oxygen atoms and/or nitrogen atoms;

a is an integer of from 0 to 3;

$R^1$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where a is greater than 1, each substituent $R^1$ may be the same or different;

b is an integer of from 0 to 4;

$R^2$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where b is greater than 1, each substituent $R^2$ may be the same or different;

W is selected from the group consisting of $NR^{4a}$, O, S, S=O, $SO_2$ or $C(R^{4a}R^{4b})_2$, wherein $R^{4a}$ and $R^{4b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms;

Y and Z are the same or different and each is a substituent selected from the group consisting of $(CR^{5a}R^{5b})_{n1}$, C=O, $SO_2$, $C(=O)NR^{5a}$, $C(=O)NR^{5a}SO_2$ and $C=O(R^{5a}R^{5b})_{n2}$, wherein n1 and n2 are the same or different and each is 0 or 1 and $R^{5a}$ and $R^{5b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms; and V is selected from the group consisting of $(CR^{3a}R^{3b})_pSO_2N(R^{3b})X$ and $(CR^{3a}R^{3b})_pN(R^{3b})SO_2X$, wherein p is an integer of from 0 to 2, $R^{3a}$ and $R^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms which may optionally be substituted with at least one substituent selected from alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, carbonyl groups, hydroxyl groups and cyano groups, and 5- to 7-membered aromatic heterocyclic groups containing from 1 to 3 sulfur atoms, oxygen atoms and/or nitrogen atoms, and X is a substituent selected from the group consisting of hydroxyalkyl groups having from 1 to 6 carbon atoms, alkoxyalkyl groups comprising alkyl groups having from 1 to 6 carbon atoms which are substituted with alkoxy groups having from 1 to 6 carbon atoms, haloalkoxyalkyl groups comprising alkyl groups having from 1 to 6 carbon atoms which are substituted with haloalkoxy groups having from 1 to 6 carbon atoms, aryloxyalkyl groups comprising alkyl groups having from 1 to 6 carbon atoms which are substituted with aryloxy groups having from 5 to 14 carbon atoms which may optionally be substituted with at least one substituent selected from alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups and cyano groups, polyalkylene glycol residues of general formula $HO-[(CR^{6a}R^{6b})_{c1}-O-(CR^{6c}R^{6d})_{c2}]_{c3}-$ wherein c1 and c2 are the same or different and each is an integer of from 0 to 4, c3 is an integer of from 1 to 20 and $R^{6a}$, $R^{6b}$, $R^{6c}$ and $R^{6d}$ may be the same or different from each other and each is a hydrogen atom or an alkyl group having from 1 to 6 carbon atoms, aminoalkyl groups having from 1 to 6 carbon atoms, monalkylaminoalkyl groups comprising an aminoalkyl group having from 1 to 6 carbon atoms that is substituted on the nitrogen atom with an alkyl group having from 1 to 6 carbon atoms and a dialkylaminoalkyl groups comprising an aminoalkyl group having from 1 to 6 carbon atoms that is substituted on the nitrogen atom with two alkyl groups that may be the same or different and each is an alkyl group having from 1 to 6 carbon atoms, and alkyl groups having from 1 to 6 carbon atoms that are substituted with one or more groups of formula NR8R9 wherein R8 and R9 together with the nitrogen atom to which they are attached form a saturated or partially unsaturated heterocyclic group which optionally contains at least one more heteroatom selected from nitrogen, oxygen and sulphur atoms (said saturated or partially unsaturated heterocyclic group optionally further being substituted by one or more substituents selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups having from 2 to 7 carbon atoms, carboxyl groups, nitro groups, amino groups, monoalkylamino groups wherein the alkyl group has from 1 to 6 carbon atoms, dialkylamino groups wherein each alkyl group is the same or different and has from 1 to 6 carbon atoms and hydroxyl groups);

(27) a compound according to (1) or a pharmacologically acceptable salt or pro-drug thereof, wherein:

$Ar^1$ and $Ar^2$ are the same or different and each is an aryl group having from 6 to 10 carbon atoms or a 5- or 6-membered aromatic heterocyclic group containing 1 or 2 sulfur atoms, oxygen atoms and/or nitrogen atoms;

a is 0 or 1;

$R^1$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent $R^1$ may be the same or different;

b is an integer of from 0 to 3;

$R^2$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where b is greater than 1, each substituent $R^2$ may be the same or different;

W is selected from the group consisting of $NR^{4a}$, O or S, wherein $R^{4a}$ is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms;

Y and Z are the same or different and each is a substituent selected from the group consisting of $(CR^{5a}R^{5b})_{n1}$, C=O and $C=O(R^{5a}R^{5b})_{n2}$, wherein n1 and n2 are the same or different and each is 0 or 1 and $R^{5a}$ and $R^{5b}$ are the same or different and each is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms; and V is a group of formula of $(CR^{3a}R^{3b})_pSO_2N(R^{3b})X$, wherein p is an integer of 0 or 1, $R^{3a}$ and $R^{3b}$ are the same or different and each is selected from the group consisting of hydrogen atoms and alkyl groups having from 1 to 4 carbon atoms, and X is a substituent selected from the group consisting of hydroxyalkyl groups having from 1 to 4 carbon atoms and polyalkylene glycol residues of general formula HO—[(CR$^{6a}$R$^{6b}$)$_{c1}$—O—(CR$^{6c}$R$^{6d}$)$_{c2}$]$_{c3}$— wherein c1 and c2 are the same or different and each is an integer of from 1 to 3, c3 is an integer of from 1 to 10 and R$^{6a}$, R$^{6b}$, R$^{6c}$ and R$^{6d}$ may be the same or different and each is a hydrogen atom or an alkyl group having from 1 to 4 carbon atoms;

(28) a compound according to (1) or a pharmacologically acceptable salt or pro-drug thereof, wherein:

Ar$^1$ and Ar$^2$ are each phenyl;

a is 0 or 1;

R$^1$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent R$^1$ may be the same or different;

b is 0 to 3;

R$^2$ is selected from the group consisting of alkyl groups having from 1 to 3 carbon atoms, halogen atoms, haloalkyl groups having from 1 to 3 carbon atoms, alkoxy groups having from 1 to 3 carbon atoms, carboxyl groups, amino groups, hydroxyl groups and cyano groups;

W is a group of formula NR$^{4a}$, wherein R$^{4a}$ is selected from the group consisting of hydrogen atoms, alkyl groups having from 1 to 3 carbon atoms and phenyl groups;

Y and Z are each a group of formula (CR$^{5a}$R$^{5b}$)$_{n1}$ wherein each n1 is 0; and V is a group of formula of (CR$^{3a}$R$^{3b}$)$_p$SO$_2$N(R$^{3b}$)X, wherein p is an integer of 0 or 1, each of R$^{3a}$ and R$^{3b}$ is a hydrogen atom, and X is a hydroxyalkyl group having from 1 to 4 carbon atoms or a polyalkylene glycol residue of general formula HO—[(CR$^{6a}$R$^{6b}$)$_{c1}$—O—(CR$^{6b}$R$^{6d}$)$_{c2}$]$_{c3}$— wherein c1 and c2 are the same or different and each is 1 or 2, c3 is an integer of from 1 to 6 and each of R$^{6a}$, R$^{6b}$, R$^{6c}$ and R$^{6d}$ is a hydrogen atom;

(29) a compound according to (1) or a pharmacologically acceptable salt or pro-drug thereof, wherein:

Ar$^1$ and Ar$^2$ are the same or different and each is an aryl group having from 5 to 14 carbon atoms or a 5- to 7-membered aromatic heterocyclic group containing from 1 to 3 sulfur atoms, oxygen atoms and/or nitrogen atoms;

a is an integer of from 0 to 3;

R$^1$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where a is greater than 1, each substituent R$^1$ may be the same or different;

b is an integer of from 0 to 4;

R$^2$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where b is greater than 1, each substituent R$^2$ may be the same or different;

W is selected from the group consisting of NR$^{4a}$, O, S, S=O, SO$_2$ or C(R$^{4a}$R$^{4b}$)$_2$, wherein R$^{4a}$ and R$^{4b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms; and V is selected from the group consisting of (CR$^{3a}$R$^{3b}$)$_p$SO$_2$N(R$^{3b}$)X and (CR$^{3a}$R$^{3b}$)$_p$N(R$^{3b}$)SO$_2$X, wherein V is selected from the group consisting of (CR$^{3a}$R$^{3b}$)$_p$SO$_2$N (R$^{3b}$)X and (CR$^{3a}$R$^{3b}$)$_p$N(R$^{3b}$)SO$_2$X, wherein p is an integer of from 0 to 2, R$^{3a}$ and R$^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms, and X is a substituent selected from the group consisting of hydroxyalkyl groups having from 1 to 6 carbon atoms, polyalkylene glycol) residues of general formula HO—[(CR$^{6a}$R$^{6b}$)$_{c1}$—O—(CR$^{6c}$R$^{6d}$)$_{c2}$]$_{c3}$—wherein c1 and c2 are the same or different and each is an integer of from 0 to 4, c3 is an integer of from 1 to 20 and R$^{6a}$, R$^{6b}$, R$^{6c}$ and R$^{6d}$ may be the same or different from each other and each is a hydrogen atom or an alkyl group having from 1 to 6 carbon atoms, aminoalkyl groups having from 1 to 6 carbon atoms, monalkylaminoalkyl groups comprising an aminoalkyl group having from 1 to 6 carbon atoms that is substituted on the nitrogen atom with an alkyl group having from 1 to 6 carbon atoms and a dialkylaminoalkyl groups comprising an aminoalkyl group having from 1 to 6 carbon atoms that is substituted on the nitrogen atom with two alkyl groups that may be the same or different and each is an alkyl group having from 1 to 6 carbon atoms;

(30) 1-[2-(2,6-Dichlorophenylamino)phenyl]-N-[2-(2-hydroxyethoxy)ethyl]-methanesulfonamide, N-[2-(2-hydroxyethoxy)ethyl]-C-[2-(2,4,6-trichlorophenylamino)phenyl]-methanesulfonamide, C-[2-(2,6-dichloro-4-trifluoromethylphenylamino)phenyl]-N-[2-(2-hydroxyethoxy)ethyl]methanesulfonamide, C-[2-(2,6-dichloro-3-methylphenylamino)phenyl]-N-{2-(2-hydroxyethoxy)-ethyl]methanesulfonamide, N-(2-hydroxyethyl)-C-[3-(2,4,6-trichlorophenylamino)phenyl]methane sulphonamide, N-[2-(2-hydroxyethoxy)ethyl]-C-[3-(2,4,6-trichlorophenylamino)phenyl]-methanesulfonamide, C-[3-(2,6-dichloro-4-trifluoromethylphenylamino)phenyl]-N-[2-(2-hydroxyethoxy)ethyl]methanesulfonamide, N-(2-hydroxyethyl)-2-(2,4,6-trichlorophenylamino)benzenesulfonamide,
N-(2-hydroxyethyl)-2-(2,6-dichlorophenylamino)benzenesulfonamide,
2-(2,6-dichloro-4-trifluoromethylphenylamino)-N-(2-hydroxyethyl)-benzenesulfonamide,
2-(2,6-dichloro-3-methylphenylamino)-N-(2-hydroxyethyl)-benzenesulfonamide,
2-(2,6-dichloro-4-trifluoromethylphenylamino)-N-[2-(2-hydroxyethoxy)ethyl]-benzenesulfonamide,
2-(2,6-dichloro-3-methylphenylamino)-N-[2-(2-hydroxyethoxy)ethyl]-benzenesulfonamide,
2-(3,5-dichlorophenylamino)-N-[2-(2-hydroxyethoxy)ethyl]-benzenesulfonamide,
N-[2-(2-hydroxyethoxy)ethyl]-2-(2,4,6-trichlorophenylamino)-benzenesulfonamide,
N-(2-hydroxyethyl)-3-(2,4,6-trichlorophenylamino)benzenesulfonamide,
3-(2,6-dichloro-4-trifluoromethylphenylamino)-N-(2-hydroxyethyl)-benzenesulfonamide;
2-chloro-N-(2-hydroxyethyl)-5-(2,4,6-trichlorophenylamino)-benzensulfonamide; and
2-chloro-5-(2,6-dichloro-4-trifluoromethylphenylamino)-N-(2-hydroxyethyl)-benzenesulfonamide
or a pharmacologically acceptable salt or pro-drug thereof.

In a second aspect of the present invention, there is provided a pharmaceutical composition comprising a pharmacologically acceptable diluent or carrier and an active ingredient, wherein said active ingredient is a compound according to any one of (1) to (30) or a pharmacologically acceptable salt or pro-drug thereof as an active ingredient thereof.

In a third aspect of the present invention, there is provided a compound according to any one of (1) to (30) or a pharmacologically acceptable salt or pro-drug thereof for use as a medicament.

In a fourth aspect of the present invention, there is provided use of a compound according to any one of (1) to (30) or a pharmacologically acceptable salt or pro-drug thereof in the preparation of a medicament for the prophylaxis or treatment of a disease in which KCNQ2, KCNQ3 or KCNQ2/3 channels are involved.

In a fifth aspect of the present invention, there is provided use of a compound according to any one of (1) to (30) or a pharmacologically acceptable salt or pro-drug thereof in the preparation of a medicament for the prophylaxis or treatment of a condition or disease ameliorated by KCNQ2, KCNQ3 or KCNQ2/3 channel opening.

In a sixth aspect of the present invention, there is provided use of a compound according to any one of (1) to (30) or a pharmacologically acceptable salt or pro-drug thereof in the preparation of a medicament for the prophylaxis or treatment of Lower Urinary Tract Disorders.

In an seventh aspect of the present invention, there is provided use of a compound according to any one of (1) to (30) or a pharmacologically acceptable salt or pro-drug thereof in the preparation of a medicament for the prophylaxis or treatment of Anxiety and Anxiety-Related Conditions.

In a eighth aspect of the present invention, there is provided use of a compound according to any one of (1) to (30) or a pharmacologically acceptable salt or pro-drug thereof in the preparation of a medicament for the prophylaxis or treatment of Epilepsy.

In a ninth aspect of the present invention, there is provided use of a compound according to any one of (1) to (30) or a pharmacologically acceptable salt or pro-drug thereof in the preparation of a medicament for the prophylaxis or treatment of Pain Disorders.

In a tenth aspect of the present invention, there is provided use of a compound according to any one of (1) to (30) or a pharmacologically acceptable salt or pro-drug thereof in the preparation of a medicament for the prophylaxis or treatment of Gynaecological Pain.

In a eleventh aspect of the present invention, there is provided use of a compound according to any one of (1) to (30) or a pharmacologically acceptable salt or pro-drug thereof in the preparation of a medicament for the prophylaxis or treatment of Cardiac Arrhythmias.

In a twelfth aspect of the present invention, there is provided use of a compound according to any one of (1) to (30) or a pharmacologically acceptable salt or pro-drug thereof in the preparation of a medicament for the prophylaxis or treatment of Thromboembolic Events.

In a thirteenth aspect of the present invention, there is provided use of a compound according to any one of (1) to (30) or a pharmacologically acceptable salt or pro-drug thereof in the preparation of a medicament for the prophylaxis or treatment of Cardiovascular Diseases.

In a fourteenth aspect of the present invention, there is provided use of a compound according to any one of (1) to (30) or a pharmacologically acceptable salt or pro-drug thereof in the preparation of a medicament for the prophylaxis or treatment of Disorders of the Auditory System.

In a fifteenth aspect of the present invention, there is provided use of a compound according to any one of (1) to (30) or a pharmacologically acceptable salt or pro-drug thereof in the preparation of a medicament for the prophylaxis or treatment of Migraine.

In a sixteenth aspect of the present invention, there is provided use of a compound according to any one of (1) to (30) or a pharmacologically acceptable salt or pro-drug thereof in the preparation of a medicament for the prophylaxis or treatment of Inflammatory and Immunological Diseases.

In an seventeenth aspect of the present invention, there is provided use of a compound according to any one of (1) to (30) or a pharmacologically acceptable salt or pro-drug thereof in the preparation of a medicament for the prophylaxis or treatment of Gastrointestinal Disorders.

In a eighteenth aspect of the present invention, there is provided use of a compound according to any one of (1) to (30) or a pharmacologically acceptable salt or pro-drug thereof in the preparation of a medicament for the prophylaxis or treatment of Vascular and Visceral Smooth Muscle Disorders.

In a nineteenth aspect of the present invention, there is provided use of a compound according to any one of (1) to (30) or a pharmacologically acceptable salt or pro-drug thereof in the preparation of a medicament for the prophylaxis or treatment of Cell Proliferative Disorders.

In a twentieth aspect of the present invention, there is provided use of a compound according to any one of (1) to (30) or a pharmacologically acceptable salt or pro-drug thereof in the preparation of a medicament for the prophylaxis or treatment of Metabolic Disorders.

In a twenty-first aspect of the present invention, there is provided use of a compound according to any one of (1) to (30) or a pharmacologically acceptable salt or pro-drug thereof in the preparation of a medicament for the prophylaxis or treatment of Memory Loss.

In a twenty-second aspect of the present invention, there is provided use of a compound according to any one of (1) to (30) or a pharmacologically acceptable salt or pro-drug thereof in the preparation of a medicament for the prophylaxis or treatment of CNS-Mediated Motor Dysfunction Disorders.

In a twenty-third aspect of the present invention, there is provided use of a compound according to any one of (1) to (30) or a pharmacologically acceptable salt or pro-drug thereof in the preparation of a medicament for the prophylaxis or treatment of Ophthalmic Disorders.

In an twenty-fourth aspect of the present invention, there is provided a method for the prophylaxis or treatment of a disease in which KCNQ2, KCNQ3 or KCNQ2/3 is involved comprising administering to a patient in need thereof an effective amount of a compound according to any one of (1) to (30) or a pharmacologically acceptable salt or pro-drug thereof.

In a twenty-fifth aspect of the present invention, there is provided a method for the prophylaxis or treatment of a condition or disease ameliorated by KCNQ2, KCNQ3 or KCNQ2/3 channel opening comprising administering to a patient in need thereof an effective amount of a compound according to any one of (1) to (30) or a pharmacologically acceptable salt or pro-drug thereof.

In a twenty-sixth aspect of the present invention, there is provided a method for the prophylaxis or treatment of Lower Urinary Tract Disorders comprising administering to a patient in need thereof an effective amount of a compound according to any one of (1) to (30) or a pharmacologically acceptable salt or pro-drug thereof.

In a twenty-seventh aspect of the present invention, there is provided a method for the prophylaxis or treatment of Anxiety and Anxiety-Related Conditions comprising administering to a patient in need thereof an effective amount of a compound according to any one of (1) to (30) or a pharmacologically acceptable salt or pro-drug thereof.

In a twenty-eighth aspect of the present invention, there is provided a method for the prophylaxis or treatment of Epilepsy comprising administering to a patient in need thereof an effective amount of a compound according to any one of (1) to (30) or a pharmacologically acceptable salt or pro-drug thereof.

In a twenty-ninth aspect of the present invention, there is provided a method for the prophylaxis or treatment of Pain Disorders comprising administering to a patient in need thereof an effective amount of a compound according to any one of (1) to (30) or a pharmacologically acceptable salt or pro-drug thereof.

In a thirtieth aspect of the present invention, there is provided a method for the prophylaxis or treatment of Gynaecological Pain comprising administering to a patient in need thereof an effective amount of a compound according to any one of (1) to (30) or a pharmacologically acceptable salt or pro-drug thereof.

In a thirty-first aspect of the present invention, there is provided a method for the prophylaxis or treatment of Cardiac Arrhythmias comprising administering to a patient in need thereof an effective amount of a compound according to any one of (1) to (30) or a pharmacologically acceptable salt or pro-drug thereof.

In a thirty-second aspect of the present invention, there is provided a method for the prophylaxis or treatment of Thromboembolic Events comprising administering to a patient in need thereof an effective amount of a compound according to any one of (1) to (30) or a pharmacologically acceptable salt or pro-drug thereof.

In a thirty-third aspect of the present invention, there is provided a method for the prophylaxis or treatment of Cardiovascular Diseases comprising administering to a patient in need thereof an effective amount of a compound according to any one of (1) to (30) or a pharmacologically acceptable salt or pro-drug thereof.

In a thirty-fourth aspect of the present invention, there is provided a method for the prophylaxis or treatment of Disorders of the Auditory System comprising administering to a patient in need thereof an effective amount of a compound according to any one of (1) to (30) or a pharmacologically acceptable salt or pro-drug thereof.

In a thirty-fifth aspect of the present invention, there is provided a method for the prophylaxis or treatment of Migraine comprising administering to a patient in need thereof an effective amount of a compound according to any one of (1) to (30) or a pharmacologically acceptable salt or pro-drug thereof.

In a thirty-sixth aspect of the present invention, there is provided a method for the prophylaxis or treatment of Inflammatory and Immunological Diseases comprising administering to a patient in need thereof an effective amount of a compound according to any one of (1) to (30) or a pharmacologically acceptable salt or pro-drug thereof.

In a thirty-seventh aspect of the present invention, there is provided a method for the prophylaxis or treatment of Gastrointestinal Disorders comprising administering to a patient in need thereof an effective amount of a compound according to any one of (1) to (30) or a pharmacologically acceptable salt or pro-drug thereof.

In a thirty-eighth aspect of the present invention, there is provided a method for the prophylaxis or treatment of Vascular and Visceral Smooth Muscle Disorders comprising administering to a patient in need thereof an effective amount of a compound according to any one of (1) to (30) or a pharmacologically acceptable salt or pro-drug thereof.

In a thirty-ninth aspect of the present invention, there is provided a method for the prophylaxis or treatment of Cell Proliferative Disorders comprising administering to a patient in need thereof an effective amount of a compound according to any one of (1) to (30) or a pharmacologically acceptable salt or pro-drug thereof.

In a fortieth aspect of the present invention, there is provided a method for the prophylaxis or treatment of Metabolic Disorders comprising administering to a patient in need thereof an effective amount of a compound according to any one of (1) to (30) or a pharmacologically acceptable salt or pro-drug thereof.

In a forty-first aspect of the present invention, there is provided a method for the prophylaxis or treatment of Memory Loss comprising administering to a patient in need thereof an effective amount of a compound according to any one of (1) to (30) or a pharmacologically acceptable salt or pro-drug thereof.

In a forty-second aspect of the present invention, there is provided a method for the prophylaxis or treatment of CNS-Mediated Motor Dysfunction Disorders comprising administering to a patient in need thereof an effective amount of a compound according to any one of (1) to (30) or a pharmacologically acceptable salt or pro-drug thereof.

In a forty-third aspect of the present invention, there is provided a method for the prophylaxis or treatment of Ophthalmic Disorders comprising administering to a patient in need thereof an effective amount of a compound according to any one of (1) to (30) or a pharmacologically acceptable salt or pro-drug thereof.

In a forty-fourth aspect of the present invention, there is provided a compound according to any one of (1) to (30) or a pharmacologically acceptable salt or pro-drug thereof for use in the prophylaxis or treatment of any disease or condition recited in any of the fourth to twenty-fourth aspects of the invention recited above.

In a forty-fifth aspect of the present invention there is provided a pharmaceutical composition comprising a pharmacologically acceptable diluent or carrier and at least two active ingredients, wherein said active ingredients comprise at least one compound according to any one of (1) to (30) or a pharmacologically acceptable salt or prodrug thereof in combination at least one compound selected from the group consisting of muscarinic receptor antagonists, β3 adrenergic receptor agonists, neurokinin K receptor antagonists, vanilloid VR1 agonists, calcium channel α2 δ ligands, potassium channel activators, calcium channel inhibitors, sodium channel blockers, serotonin and norepinephrine reuptake inhibitors (SNRIs), 5-HT antagonists, alpha-1 adrenoceptor antagonists, tricyclic antidepressants, N-methyl-D-aspartate (NMDA) receptor antagonists, cannabinoid receptor agonists, anti-convulsants, aldose reductase inhibitors, opioids, alpha adrenoceptor agonists, P2X receptor antagonists, acid-sensing ion channel modulators, NGF receptor modulators, nicotinic acetylcholine receptor modulators, synaptic vesicle protein 2A ligands and non-steroidal anti-inflammatory drugs (NSAIDs).

Preferred pharmaceutical combinations according to the forty-fifth aspect of the present invention include:

(1) a pharmaceutical composition comprising a pharmacologically acceptable diluent or carrier and a combination of active ingredients, wherein said active ingredients comprise at least one compound according to any one of (1) to (30) or a pharmacologically acceptable salt or prodrug thereof in combination with at least one compound selected from the group consisting of muscarinic receptor antagonists, β3 adrenergic receptor agonists, neurokinin K receptor antagonists, vanilloid VR1 agonists, calcium channel α2 δ ligands, potassium channel activators, calcium channel inhibitors, sodium channel blockers, serotonin and norepinephrine reuptake inhibitors (SNRIs), 5-HT antagonists and α-1 adrenoceptor antagonists; and (2) a pharmaceutical composition comprising a pharmacologically acceptable diluent or carrier and a combination of active ingredients, wherein said active ingredients comprise at least one compound according to any one of (1) to (30) or a pharmacologically acceptable salt or prodrug thereof in combination with at least one compound selected from the group consisting of neurokinin K receptor antagonists, vanilloid VR1 agonists, calcium channel α2 δ ligands, potassium channel activators, calcium channel inhibitors, sodium channel blockers, serotonin and norepinephrine reuptake inhibitors (SNRIs), tricyclic antidepressants, N-methyl-D-aspartate (NMDA) receptor antagonists, cannabinoid receptor agonists, anti-convulsants, aldose reductase inhibitors, opioids, alpha adrenoceptor agonists, P2X receptor antagonists, acid-sensing ion channel modulators, NGF receptor modulators, nicotinic acetylcholine receptor modulators, synaptic vesicle protein 2A ligands and non-steroidal anti-inflammatory drugs (NSAIDs).

The combinations of preferred option (1) are of particular use in the prophylaxis or treatment of lower urinary tract disorders. The combinations of preferred option (2) are of particular use in the prophylaxis or treatment of pain.

In a forty-sixth aspect of the present invention there is provided use of at least one compound according to any one of (1) to (30) or a pharmacologically acceptable salt or prodrug thereof and at least one compound selected from the group consisting of muscarinic receptor antagonists, β3 adrenergic receptor agonists, neurokinin K receptor antagonists, vanilloid VR1 agonists, calcium channel α2 δ delta ligands, potassium channel inhibitors, calcium channel inhibitors, sodium channel blockers, serotonin and norepinephrine reuptake inhibitors (SNRIs), 5-HT antagonists and α-1 adrenoceptor antagonists in the manufacture of a medicament for the prophylaxis or treatment of lower urinary tract disorders.

In a forty-seventh aspect of the present invention there is provided use of at least one compound according to any one of (1) to (30) or a pharmacologically acceptable salt or prodrug thereof and at least one compound selected from the group consisting of neurokinin K receptor antagonists, vanilloid VR1 agonists, calcium channel α2 δ delta ligands, potassium channel inhibitors, calcium channel inhibitors, sodium channel blockers, serotonin and norepinephrine reuptake inhibitors (SNRIs), tricyclic antidepressants, N-methyl-D-aspartate (NMDA) receptor antagonists, cannabinoid receptor agonists, anti-convulsants, aldose reductase inhibitors, opioids, alpha adrenoceptor agonists, P2X receptor antagonists, acid-sensing ion channel modulators, NGF receptor modulators, nicotinic acetylcholine receptor modulators, synaptic vesicle protein 2A ligands and non-steroidal anti-inflammatory drugs (NSAIDs) in the manufacture of a medicament for the prophylaxis or treatment of pain.

DETAILED DESCRIPTION OF THE INVENTION

In the compounds of the present invention, the alkyl groups in the definitions of $R^1$, $R^2$, $R^{3a}$, $R^{3b}$, $R^{4a}$, $R^{4b}$, $R^{5a}$, $R^{5b}$, $R^{6a}$ $R^{6b}$, $R^{6c}$ and $R^{6d}$ are preferably alkyl groups having from 1 to 6 carbon atoms, more preferably alkyl groups having from 1 to 4 carbon atoms and most preferably methyl groups.

In the compounds of the present invention, the cycloalkyl groups in the definitions of $R^{3a}$, $R^{3b}$, $R^{4a}$, $R^{4b}$, $R^{5a}$ and $R^{5b}$ are preferably cycloalkyl groups having from 3 to 7 carbon atoms, more preferably having 5 or 6 carbon atoms and most preferably cyclohexyl.

In the compounds of the present invention, the aryl groups in the definitions of $Ar^1$, $Ar^2$, $R^{3a}$, $R^{3b}$, $R^{4a}$, $R^{4b}$, $R^{5a}$ and $R^{5b}$ are preferably aryl groups having from 5 to 14 carbon atoms. Examples of the unsubstiuted aryl groups include phenyl, indenyl, naphthyl, phenanthrenyl and anthracenyl groups. More preferred aryl groups include phenyl groups.

In the compounds of the present invention, the aryloxyalkyl groups in the definition of X are preferably alkyl groups having from 1 to 6 carbon atoms which are substituted with aryloxy groups having from 5 to 14 carbon atoms which may optionally be substituted with at least one substituent selected from alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups and cyano groups.

In the compounds of the present invention, the alkoxyalkyl groups in the definition of X are preferably alkyl groups having from 1 to 6 carbon atoms which are substituted with one or more alkoxy groups having from 1 to 6 carbon atoms, more preferably alkyl groups having from 1 to 4 carbon atoms substituted with alkoxy groups having from 1 to 4 carbon atoms and most preferably methoxymethyl and 2-methoxyethyl groups.

In the compounds of the present invention, the haloalkoxyalkyl groups in the definition of X are preferably alkoxyalkyl groups as defined above in which the alkoxy moiety is substituted by one or more halogen atoms, preferred examples including trifluoromethoxymethyl and 2,2-dichloroethoxyethyl groups.

In the compounds of the present invention, the alkyl groups that are substituted with groups of formula NR8R9 wherein R8 and R9 together with the nitrogen atom to which they are attached to form a saturated or partially unsaturated heterocyclic group in the definition of X are preferably alkyl groups having from 1 to 6 carbon atoms which are substituted with one or more saturated or partially unsaturated heterocyclic groups which optionally contain at least one more heteroatom selected from nitrogen, oxygen and sulphur atoms (said saturated or partially unsaturated heterocyclic group optionally further being substituted by one or more substituents selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups having from 2 to 7 carbon atoms, carboxyl groups, carbonyl groups, nitro groups, amino groups, monoalkylamino groups wherein the alkyl group has from 1 to 6 carbon atoms, dialkylamino groups wherein each alkyl group is the same or different and has from 1 to 6 carbon atoms and hydroxyl groups).

In the compounds of the present invention, the heteroaryl groups in the definitions of $Ar^1$, $Ar^2$, $R^{3a}$, $R^{3b}$, $R^{4a}$, $R^{4b}$, $R^{5a}$ and $R^{5b}$ are preferably 5- to 7-membered aromatic heterocyclic group containing 1 to 3 sulfur atoms, oxygen atoms and/or nitrogen atoms. Examples include furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl and pyrazinyl groups. More preferred heteroaryl groups include furyl, thienyl, pyrrolyl and pyridyl.

In the compounds of the present invention, the alkoxy groups in the definitions of $R^1$ and $R^2$ are preferably alkoxy groups having from 1 to 6 carbon atoms, more preferably alkoxy groups having from 1 to 4 carbon atoms and most preferably methoxy or ethoxy groups.

In the compounds of the present invention, the haloalkyl groups in the definitions of $R^1$ and $R^2$ are preferably alkyl groups as defined above that are substituted with one or more halogen atoms. More preferably, they are alkyl groups having from 1 to 4 carbon atoms that are substituted with at least one chlorine or fluorine atom and most preferably they are chloromethyl group, trichloromethyl groups, trifluoromethyl groups and tetrafluoroethyl groups.

In the compounds of the present invention, the alkoxycarbonyl groups in the definitions of $R^1$ and $R^2$ are preferably carbonyl groups substituted with alkoxy groups as defined above, and are more preferably methoxycarbonyl or ethoxycarbonyl groups.

In the compounds of the present invention, the hydroxyalkyl groups in the definitions of X are preferably alkyl groups as defined above that are substituted with one or more hydroxy groups, and are more preferably hydroxymethyl, 1-hydroxyethyl or 2-hydroxyethyl groups.

In the compounds of the present invention, the monalkylamino groups in the definitions of $R^1$ and $R^2$ are preferably amino groups which are substituted with one alkyl group as defined above, and are more preferably methylamino, ethylamino or t-butylamino groups.

In the compounds of the present invention, the dialkylamino groups in the definitions of $R^1$ and $R^2$ are preferably amino groups which are substituted with two alkyl groups as defined above which may be the same or different from each other, and are more preferably dimethylamino or diethylamino groups.

In the compounds of the present invention, the acylamino groups in the definitions of $R^1$ and $R^2$ are preferably amino groups which are substituted with an acyl group having from 1 to 6 carbon atoms and are more preferably acetylamino or propionylamino groups.

In the compounds of the present invention, the alkoxycarbonylamino groups in the definitions of $R^1$ and $R^2$ are preferably amino groups which are substituted with an alkoxycarbonyl group as defined above, and are more preferably methoxycarbonylamino or ethoxycarbonylamino groups.

In the compounds of the present invention, the alkylsulphonyl groups in the definitions of $R^1$ and $R^2$ are preferably sulphonyl groups which are substituted with an alkyl group as defined above and are more preferably a methylsulphonyl or ethylsulphonyl group.

In the compounds of the present invention, the alkylsulphonylamino groups in the definitions of $R^1$ and $R^2$ are preferably sulphonylamino groups which are substituted with an alkyl group as defined above and are more preferably a methylsulphonylamino or ethylsulphonylamino group.

In the compounds of the present invention, the polyalkylene glycol residues in the definition of X are preferably groups of formula $HO-[(CR^{6a}R^{6b})_{c1}-O-(CR^{6c}R^{6d})_{c2}]_{c3}-$, wherein c1 and c2 are the same or different and each is an integer of from 0 to 4, c3 is an integer of from 1 to 20 and $R^{6a}$, $R^{6b}$, $R^{6c}$ and $R^{6d}$ may be the same or different and each is a hydrogen atom or an alkyl group having from 1 to 6 carbon atoms; more preferably groups of formula $HO-[(CR^{6a}R^{6b})_{c1}-O-(CR^{6c}R^{6d})_{c2}]_{c3}-$, wherein c1 and c2 are the same or different and each is an integer of from 1 to 3, c3 is an integer of from 1 to 10 and $R^{6a}$, $R^{6b}$, $R^{6c}$ and $R^{6d}$ may be the same or different and each is a hydrogen atom or an alkyl group having from 1 to 4 carbon atoms; and most preferably groups of formula $HO-[(CR^{6a}R^{6b})_{c1}-O-(CR^{6a}R^{6b})_{c1}-O-(CR^{6c}R^{6d})_{c2}]_{c3}-$, wherein c1 and c2 are the same or different and each is 1 or 2, c3 is an integer of from 1 to 6 and each of $R^{6a}$, $R^{6b}$, $R^{6c}$ and $R^{6d}$ is the same or different and is a hydrogen atom.

In the compounds of the present invention, the aminoalkyl groups in the definition of X are preferably alkyl groups as defined above that are substituted with one ore more amino groups, and are more preferably aminomethyl, 1-aminoethyl or 2-aminoethyl groups.

In the compounds of the present invention, the monoalkylaminoalkyl groups in the definition of X are preferably alkyl groups as defined above that are substituted with one ore more monoalkylamino groups as defined above, and are more preferably methylaminomethyl, ethylaminomethyl, 1 methylaminoethyl or 2-methylaminoethyl groups.

In the compounds of the present invention, dialkylalkylaminoalkyl groups in the definition of X are preferably alkyl groups as defined above that are substituted with one ore more dialkylamino groups as defined above, and are more preferably dimethylaminomethyl or 2-dimethylaminoethyl groups.

The compounds of formula (1) of the present invention can form pharmacologically acceptable salts and these form a part of the present invention. Examples of such salts include inorganic salts such as ammonium salts; organic amine salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-N-phenethylamine salts, piperazine salts, tetramethylammonium salts and tris(hydroxymethyl) aminemethane salts; hydrohalogenated salts such as hydrofluoric acid salts, hydrochlorides, hydrobromides and hydroiodides; inorganic acid salts such as nitrates, perchlorates, sulfates and phosphates; lower alkanesulfonate salts such as methanesulfonates, trifluoromethanesulfonates and ethanesulfonates; arylsulfonate salts such as benzensulfonates and p-toluenesulfonates; organic acid salts such as acetates, malates, fumarates, succinates, citrates, tartrates, oxalates and maleates; and amino acid salts such as ornithinates, glutamates and aspartates. Of these, organic amine salts are more preferred and triethylamine salts are most preferred.

The compounds of formula (1) of the present invention can be administered in the form of prodrugs. Prodrugs are derivatives of the pharmacologically active compound in which one or more of the substituents on said compound are protected by a group which is then removable by a biological process (e.g. hydrolysis) in vivo after administration to the patient. Many suitable prodrugs are well-known to the person in the art and can be found, for example, in "Greene's Protective Groups in Organic Synthesis", 4$^{th}$ Edition, 2006, Wiley-VCH. Suitable examples of such prodrugs include pharmacologically acceptable esters of the compound having the formula (1) wherein a carboxyl moiety of the compound having the formula (1) is esterified. The pharmacologically acceptable esters are not particularly restricted, and can be selected by a person with an ordinary skill in the art. In the case of said esters, it is preferable that such esters can be cleaved by a biological process such as hydrolysis in vivo. The group constituting the said esters (the group shown as R when the esters thereof are expressed as —COOR) can be, for example, a $C_1$-$C_4$ alkoxy $C_1$-$C_4$ alkyl group such as methoxyethyl, 1-ethoxyethyl, 1-methyl-1-methoxyethyl, 1-(isopropoxy) ethyl, 2-methoxyethyl, 2-ethoxyethyl, 1,1-dimethyl-1-methoxymethyl, ethoxymethyl, propoxymethyl, isopropoxymethyl, butoxymethyl or t-butoxymethyl; a $C_1$-$C_4$ alkoxylated $C_1$-$C_4$ alkoxy $C_1$-$C_4$alkyl group such as 2-methoxyethoxymethyl; a $C_6$-$C_{10}$ aryloxy $C_1$-$C_4$ alkyl group such as phenoxymethyl; a halogenated $C_1$-$C_4$ alkoxy $C_1$-$C_4$ alkyl group such as 2,2,2-trichloroethoxymethyl or bis(2-chloroethoxy)methyl; a $C_1$-$C_4$ alkoxycarbonyl $C_1$-$C_4$ alkyl group such as methoxycarbonylmethyl; a cyano $C_1$-$C_4$ alkyl group such as cyanomethyl or 2-cyanoethyl; a $C_1$-$C_4$ alkylthiomethyl group such as methylthiomethyl or ethylthiomethyl; a $C_6$-$C_{10}$ arylthioethyl group such as phenylthiomethyl or naphthylthiomethyl; a $C_1$-$C_4$ alkylsulfonyl $C_1$-$C_4$ lower alkyl group, which may be optionally substituted with a halogen atom(s) such as 2-methanesulfonylethyl or 2-trifluoromethanesulfonylethyl; a $C_6$-$C_{10}$ arylsulfonyl $C_1$-$C_4$ alkyl group such as 2-benzenesulfonylethyl or 2-toluenesulfonylethyl; a $C_1$-$C_7$ aliphatic acyloxy $C_1$-$C_4$ alkyl group such as formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl; a $C_5$-$C_6$ cycloalkylcarbonyloxy $C_1$-$C_4$ alkyl group such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl or 1-cyclohexylcarbonyloxybutyl; a $C_6$-$C_{10}$ arylcarbonyloxy $C_1$-$C_4$ alkyl group such as benzoyloxymethyl; a $C_1$-$C_6$ alkoxycarbonyloxy $C_1$-$C_4$ alkyl group such as methoxycarbonyloxymethyl, 1-(methoxycarbonyloxy)ethyl, 1-(methoxycarbonyloxy)propyl, 1-(methoxycarbonyloxy)butyl, 1-(methoxycarbonyloxy)pentyl, 1-(methoxycarbonyloxy) hexyl, ethoxycarbonyloxymethyl, 1-(ethoxycarbonyloxy) ethyl, 1-(ethoxycarbonyloxy)propyl, 1-(ethoxycarbonyloxy) butyl, 1-(ethoxycarbonyloxy)pentyl, 1-(ethoxycarbonyloxy) hexyl, propoxycarbonyloxymethyl, 1-(propoxycarbonyloxy) ethyl, 1-(propoxycarbonyloxy)propyl, 1-(propoxycarbonyloxy)butyl, isopropoxycarbonyloxymethyl, 1-(isopropoxycarbonyloxy)ethyl, 1-(isopropoxycarbonyloxy)butyl, butoxycarbonyloxymethyl, 1-(butoxycarbonyloxy)ethyl, 1-(butoxycarbonyloxy)propyl, 1-(butoxycarbonyloxy)butyl, isobutoxycarbonyloxymethyl, 1-(isobutoxycarbonyloxy)ethyl, 1-(isobutoxycarbonyloxy) propyl, 1-(isobutoxycarbonyloxy)butyl, t-butoxycarbonyloxymethyl, 1-(t-butoxycarbonyloxy)ethyl, pentyloxycarbonyloxymethyl, 1-(pentyloxycarbonyloxy)ethyl, 1-(pentyloxycarbonyloxy)propyl, hexyloxycarbonyloxymethyl, 1-(hexyloxycarbonyloxy)ethyl or 1-(hexyloxycarbonyloxy)propyl; a $C_5$-$C_6$ cycloalkyloxycarbonyloxy $C_1$-$C_4$ alkyl group such as cyclopentyloxycarbonyloxymethyl, 1-(cyclopentyloxycarbonyloxy)ethyl, 1-(cyclopentyloxycarbonyloxy)propyl, 1-(cyclopentyloxycarbonyloxy)butyl, cyclohexyloxycarbonyloxymethyl, 1-(cyclohexyloxycarbonyloxy)ethyl, 1-(cyclohexyloxycarbonyloxy)propyl or 1-(cyclohexyloxycarbonyloxy)butyl; a [5-($C_1$-$C_4$ alkyl)-2-oxo-1, 3-dioxolen-4-yl]methyl group such as (5-methyl-2-oxo-1,3-dioxolen-4-yl)methyl, (5-ethyl-2-oxo-1,3-dioxolen-4-yl) methyl, (5-propyl-2-oxo-1,3-dioxolen-4-yl)methyl, (5-isopropyl-2-oxo-1,3-dioxolen-4-yl)methyl or (5-butyl-2-oxo-1,3-dioxolen-4-yl)methy; a [5-(phenyl, which may be optionally substituted with a $C_1$-$C_4$ alkyl, $C_1$-$C_4$ alkoxy or halogen atom(s))-2-oxo-1,3-dioxolen-4-yl]methyl group such as (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl or [5-(4-chlorophenyl)-2-oxo-1,3-dioxolen-4-yl]methyl; or a phthalidyl group, which may be optionally substituted with a $C_1$-$C_4$ alkyl or $C_1$-$C_4$ alkoxy group(s), such as phthalidyl, dimethylphthalidyl or dimethoxyphthalidyl, and is preferably a pivaloyloxymethyl group, phthalidyl group or (5-methyl-2-oxo-1,3-dioxolen-4-yl)methyl group, and more preferably a (5-methyl-2-oxo-1,3-dioxolen-4-yl)methyl group.

The compounds of formula (1) or pharmacologically active prodrugs or salts thereof contain some substituents for which there exist isosteres, and compounds containing such isosteres in place of said substituents also form a part of the present invention. For example, where the compounds of formula (1) or pharmacologically active prodrugs or salts thereof contain a carboxyl group, this can be replaced with a tetrazolyl group.

Hydrates or solvates of the compounds of formula (1), prodrugs thereof and pharmacologically acceptable salts thereof can also be used and form a part of the invention.

Some compounds of formula (1) and their pharmacologically acceptable salts or prodrugs thereof of the present invention may have one or more asymmetric carbons, and optical isomers (including diastereoisomers) due to the presence of asymmetric carbon atom(s) in the molecule can exist. These respective isomers are included in the present invention, both as individual isomers and mixtures thereof in all possible ratios.

Examples of the administration form of a compound having the general formula (I) of the present invention, or pharmacologically acceptable salt or prodrug thereof, include oral administration by tablets, capsules, granules, powders or syrups, and parenteral administration by injection, patches or suppositories. Moreover, a compound having the general formula (I) or a pharmacologically acceptable salt or prodrug thereof of the present invention can also be administered by pulmonary administration in the form of a powder, solution or suspension. Preparations for these administrations are produced by known methods using additives such as excipients, lubricants, binders, disintegrants, stabilizers, corrigents, diluents and so forth.

Examples of excipients include organic excipients such as sugar derivatives, e.g. lactose, sucrose, glucose, mannitol or sorbitol, starch derivatives, e.g. corn starch, potato starch, α-starch, dextrin or carboxymethyl starch, cellulose derivatives, e.g. crystalline cellulose, low substituted hydroxypropyl cellulose, hydroxypropyl methyl cellulose, carboxymethyl cellulose, calcium carboxymethyl cellulose or internally crosslinked sodium carboxymethyl cellulose, and gum Arabic, dextran or pullulan; and, inorganic excipients such as silicate derivatives, e.g. light anhydrous silicic acid, synthetic aluminium silicate or magnesium aluminium metasilicate, phosphates, e.g. calcium phosphate, carbonates, e.g. calcium carbonate, or sulfates, e.g. calcium sulfate.

Examples of lubricants include stearic acid and metal stearates such as calcium stearate or magnesium stearate; talc; colloidal silica; waxes such as bee gum or spermaceti; boric acid; adipic acid; sulfates such as sodium sulfate; glycol; fumaric acid; sodium benzoate; DL-leucine; sodium fatty acid salts; lauryl sulfates such as sodium lauryl sulfate or magnesium lauryl sulfate; silicic acids such as silicic anhydride or silicate hydrate; and, starch derivatives.

Examples of binders include polyvinylpyrrolidone, Macrogol and compounds similar to the aforementioned excipients.

Examples of disintegrants agents include compounds similar to the aforementioned excipients, and chemically crosslinked starches and celluloses such as cross sodium carmellose, sodium carboxymethyl starch or crosslinked polyvinylpyrrolidone.

Examples of stabilizers include paraoxybenzoate esters such as methyl paraben or propyl paraben; alcohols such as chlorobutanol, benzyl alcohol or phenyl ethyl alcohol; benzalkonium chloride; phenols such as phenol or cresol; thimerosal; dehydroacetic acid; and, sorbic acid.

Examples of corrigents include ordinarily used sweeteners, sour flavourings and fragrances.

In the case of producing a solution or suspension for pulmonary administration of a compound having the general formula (I) or pharmacologically acceptable salt or prodrug thereof of the present invention, for example, said solution or suspension can be produced by dissolving or suspending crystals of the present invention in water or in a mixture of water and an auxiliary solvent (e.g. ethanol, propylene glycol or polyethylene glycol). Such a solution or suspension may also contain an antiseptic (e.g. benzalkonium chloride), solubilizing agent (e.g. a polysorbate such as Tween 80 or Span 80 or surface activator such as benzalkonium chloride), buffer, isotonic agent (e.g. sodium chloride), absorption promoter and/or thickener. In addition, the suspension may additionally contain a suspending agent (such as microcrystalline cellulose or sodium carboxymethyl cellulose).

A composition for pulmonary administration produced in the manner described above is administered directly into the nasal cavity or oral cavity by a typical means in the field of inhalants (using, for example, a dropper, pipette, cannula or atomizer). In the case of using an atomizer, crystals of the present invention can be atomized as an aerosol in the form of a pressurized pack together with a suitable nebula (for example, a chlorofluorocarbon such as dichlorofluoromethane, trichlorofluoromethane or dichlorotetrafluoroethane, or a gas such as carbon dioxide), or they can be administered using a nebulizer.

The amount of a compound having the general formula (I) or pharmacologically acceptable salt or prodrug thereof of the present invention used varies depending on the symptoms, age, administration method and so forth, and may be administered either in a single dose or by dividing into multiple doses according to the symptoms.

In the combinations according to the forty-seventh aspect of the present invention, typical examples of each of the classes of compounds that can be used in combination with the compounds having the general formula (I) or a pharmacologically acceptable salt or prodrug thereof of the present invention are as follows:

1. Examples of muscarinic receptor antagonists (including but not limited to selective M3 antagonists) include esoxybutynin, oxybutynin [especially the chloride], tolterodine [especially the tartrate], solifenacin [especially the succinate], darifenacin [especially the hydrobromide], temiverine, fesoterodine, imidafenacin and trospium [especially the chloride].

2. Examples of β3 adrenergic receptor agonists include YM-178 and solabegron, KUC-7483.

3. Examples of neurokinin K receptor antagonists (including selective NK-1 antagonists) include cizolirtine and casopitant.

4. Examples of vanilloid VR1 agonists include capsaicin, resiniferatoxin and NDG-8243.

5. Examples of calcium channel α2 β ligands include gabapentin and pregabalin.

6. Examples of potassium channel activators (including activators of KCNQ, BKCa channels, Kv channels and KATP channels) include KW-7158, NS-8 and retigabine.

7. Examples of calcium channel inhibitors (including Cav2.2 channel inhibitors) include ziconotide and NMED-160.

8. Examples of sodium channel blockers include lidocaine, lamotrigine, VX-409, ralfinamide and carbamazepine.

9. Examples of serotonin and norepinephrine reuptake inhibitors (SNRIs) include duloxetine and venlafaxine 10. Examples of 5-HT antagonists including 5-HT1 antagonists and 5HT3 antagonists.

11. Examples of α-1 adrenoceptor antagonists include tamsulosin.

12. Examples of tricyclic antidepressants include amitriptyline, amoxapine, clomipramine, dosulepin (dothiepin), doxepin, imipramine, lofepramine, nortriptyline, and trimipramine.

13. Examples of N-methyl-D-aspartate (NMDA) receptor antagonists include ketamine, memantine, amantadine, AVP-923, NP-1 and EVT-101.

14. Examples of cannabinoid receptor agonists include GW-1000 (Sativex) and KDS-2000.

15. Anti-convulsants. Examples include lacosamide, carbamazepine, topiramate, oxcarbazepine and levetiracetam 16. Examples of aldose reductase inhibitors include tolrestat, zopolrestat, zenarestat, epalrestat, sorbinil, AS-3201, fidarestat, risarestat, ponalrestat and alrestatin.

17. Examples of opioids (e.g. mu opioid agonists) include fentanyl and tapentadol.

18. Examples of a adrenoceptor agonists include $a_1$-adrenoceptor agonists such as ethoxamine, phenylephrine, oxymetazoline, tetrahydralazine and xylometazoline and $a_2$-adrenoceptor agonists such as clonidine, guanabenz, guanfacine and α-methyldopa.

19. Examples of P2X receptor antagonists including P2X2 receptor antagonists and P2X7 receptor antagonists.

20. Examples of acid-sensing ion channel modulators include amiloride.

21. Examples of NGF receptor modulators include trkA.

22. Examples of nicotinic acetylcholine receptor modulators include A-85380, tebanicline, ABT-366833, ABT-202, ABT-894, epibatidine analogs and SIB-1663.

23. Examples of synaptic vesicle protein 2A ligands include brivaracetam.

Examples of the administration form of the combination of the present invention are the same as given above for the compounds of general formula (I) and pharmacologically acceptable salts thereof. The particular form can be chosen depending upon the condition to be treated and the nature of the compounds being administered in combination. For example, a combination of a compound of general formula (I) or a pharmacologically acceptable salt thereof with lidocaine could be administered transdermally by means of a patch while a combination with ziconotide could be administered transmucosally.

Synthesis of the Compounds of the Invention

Compounds of formula (I) wherein $Ar^1$ and $Ar^2$ each represent phenyl groups, W is a group of formula NH, Y and Z are each single bonds and V is a group of formula $—(CR^{3a}CR^{3b})_pSO_2NR^{3b}X$ wherein X is as described above can be prepared according to the following general Reaction Scheme 1:

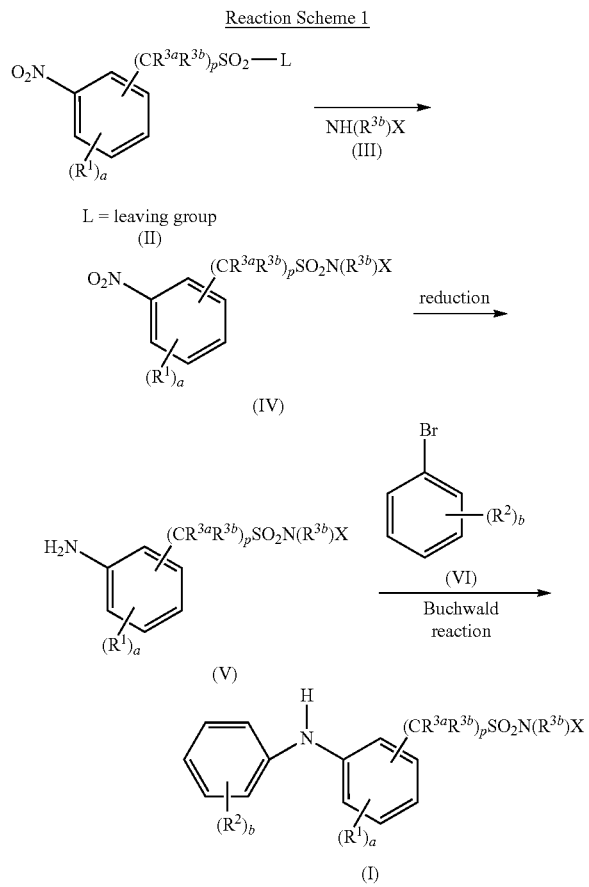

wherein $R^1$, $R^2$, $R^{3b}$, $R^{3a}$, a, b, p and X are as defined above.

The first step of Reaction Scheme 1 involves reaction of a 2-nitrophenylmethylsulfonylchloride or 2-nitrobenzenesulfonylchloride or derivative of formula (II) which has a leaving group L with an amino compound of formula (III) to give a 2-nitrophenylmethyl-sulfonamide or 2-nitrobenzenesulfonamide derivative of formula (IV). The leaving group L can be any group which readily becomes detached from the sulfur atom to which it is attached in the compound of formula (II) on nucleophilic attack by the nitrogen atom of the amino compound of formula (III). Such leaving groups are well known to the person skilled in the art and include halogen atoms, mesyl groups, tosyl groups and trifluoromethanesulfonyl groups. Chlorine atoms, iodine atoms, bromine atoms and tosyl groups are more preferred and chlorine atoms are most preferred.

The second step of Reaction Scheme 1 involves reaction of the 2-nitrophenylmethylsulfonamide or 2-nitrobenzenesulfonamide derivative of formula (IV) with a reducing agent to give the corresponding aniline derivative of formula (V). Any reducing agent suitable for the reduction of a nitro group to an amino group may be used, suitable examples of which include catalytic hydrogenation, the zinc-acetic acid method, the tin-alcohol method and the tin-hydrochloric acid method. Preferred is catalytic hydrogenation.

The final step of Reaction Scheme 1 involves reaction of the 2-aminophenyl-methylsulfonamide or 2-aminobenzenesulfonamide derivative of formula (V) with an optionally substituted halophenyl compound of formula (VI) in a Buchwald reaction utilizing appropriate palladium catalysis and ligand to give the target N-phenylanthranilic derivatives of formula (I). Most preferred are bromophenyl derivatives.

Compounds of formula (I) wherein $Ar^1$ and $Ar^2$ each represent phenyl groups, W is a group of formula $NR^{4a}$, Y and Z are each single bonds and V is a group of formula $—(CR^{3a}CR^{3b})_pSO_2NR^{3b}X$ wherein X is as described above can also be prepared according to the following general Reaction Scheme 2.

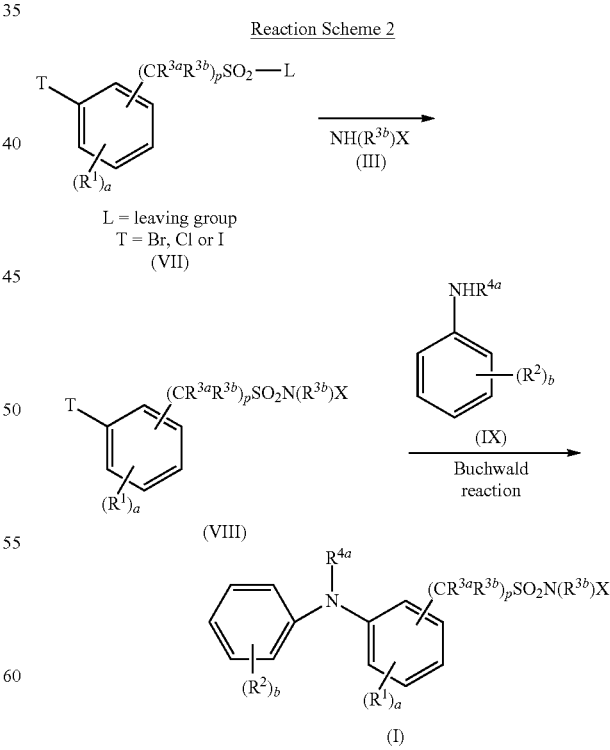

wherein $R^1$, $R^2$, $R^{3a}$, $R^{3b}$, $R^{4a}$, a, a, b, p and are as defined above.

The first step of Reaction Scheme 2 involves reaction of a 2-halophenylmethylsulfonylchloride or 2-halobenzenesulfonylchloride derivative of formula (VII) which has a leaving group L with an amino compound of formula (III) to give a 2-halophenylmethylsulfonamide or 2-halobenzenesulfonamide derivative of formula (VIII). The leaving group L can be any group which readily becomes detached from the sulfur atom to which it is attached in the compound of formula (VII) on nucleophilic attack by the nitrogen atom of the amino compound of formula (III). Such leaving groups are well known to the person skilled in the art and include halogen atoms, mesyl groups, tosyl groups and trifluoromethanesulfonyl groups. Chlorine atoms, iodine atoms, bromine atoms and tosyl groups are more preferred and chlorine atoms are most preferred.

The second and final step of Reaction Scheme 2 involves reaction of the 2-halophenylmethylsulfonamide or 2-halobenzenesulfonamide derivative of formula (VIII) with an optionally substituted aniline compound of formula (IX) in a Buchwald reaction utilizing appropriate palladium catalysis and ligand to give the target N-phenylanthranilic derivatives of formula (I).

The present invention may be further understood by consideration of the following examples, with reference to the activity of selected examples displayed in table 1:

EXAMPLES

Using the general procedure described above in Reaction Scheme 1, the following compound was prepared.

Example [01]

1-[2-(2,6-Dichlorophenylamino)phenyl]-N-[2-(2-hydroxyethoxy)ethyl]-methanesulfonamide

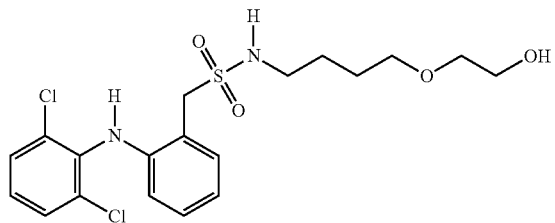 [SMILES: O=S(=O)(Cc1ccccc1Nc1c(Cl)cccc1Cl)NCCCCOCCO]

Example [01]

N-[2-(2-Hydroxyethoxy)ethyl]-1-(2-nitrophenyl)-methanesulfonamide (IV)

To a stirred solution of 2-(2-aminoethoxy)ethanol (0.557 g), 5.31 mmol) and potassium carbonate (1.17 g, 8.48 mmol) in toluene (50 ml) and water (4 ml) at room temperature, was added 2-nitro-alpha-toluenesulfonyl chloride (1.00 g, 4.24 mmol) in one portion and the reaction was left to stir overnight. The reaction was diluted with ethyl acetate and water. The organic layer was separated before being washed with brine, dried over magnesium sulfate, filtered and the filtrate concentrated in vacuo. The crude material was purified by column chromatography eluting with ethyl acetate:hexane to afford N-[2-(2-hydroxyethoxy)ethyl]-1-(2-nitrophenyl) methanesulfonamide as product (0.155 g, 12%); $R_f$ (ethyl acetate:hexane 2:1) 0.11; $\delta_H$ (400 MHz, CDCl$_3$) 8.02 (1H, d), 7.67 (2H, m), 7.53 (1H, dt), 5.15 (1H, brs), 4.86 (2H, s), 3.71 (2H, s), 3.56 (4H, m), 3.19 (2H, m) and 2.36 (1H, s); LCMS $R_t$=2.60 min, m/z (APCI) 305 (MH$^+$).

Example 1(2)

1-(2-Aminophenyl)-N-[2-(2-hydroxyethoxy)ethyl]-methanesulfonamide (V)

To a stirred solution of N-[2-(2-hydroxyethoxy)ethyl]-1-(2-nitrophenyl)-methanesulfonamide (0.145 g, 0.48 mmol) in methanol (10 ml) under an atmosphere of nitrogen was added 10% Pd/C (10 Wt %, 15 mg) in one portion. The reaction was evacuated, placed under an atmosphere of hydrogen (1 bar) and stirred vigorously overnight. The reaction was filtered through celite and the filtrate was concentrated in vacuo to afford 1-(2-aminophenyl)-N-[2-(2-hydroxyethoxy)ethyl]methanesulfonamide as product (0.105 g, 81%); LCMS $R_t$=2.06 min, m/z (APCI) 297 (M+Na).

Example 1(3)

1-[2-(2,6-Dichlorophenylamino)phenyl]-N-[2-(2-hydroxy-ethoxy)ethyl]methanesulfonamide (I)

To a stirred solution of 1-(2-aminophenyl)-N-[2-(2-hydroxyethoxy)ethyl]-methanesulfonamide (100 mg, 0.37 mmol), 1,3-dichloro-2-bromobenzene (103 mg, 0.46 mmol), K$_2$CO$_3$ (126 mg, 0.99 mmol) and XantPhos (21 mg, 0.04 mmol) in 1,4-dioxane (2 ml) under nitrogen in a microwave tube was added Pd$_2$dba$_3$ (17 mg, 0.019 mmol) in one portion and the tube sealed. The reaction was heated with stirring in a microwave at 160° C. for 30 minutes. The reaction was cooled before filtering through celite. The crude reaction mixture was purified by column chromatography eluting with ethyl acetate:hexane to afford 1-[2-(2,6-Dichlorophenylamino)phenyl]-N-[2-(2-hydroxyethoxy)-ethyl]methanesulfonamide as product (50.5 mg, 33%); $R_f$(ethyl acetate:hexane 1:1) 0.11; $\delta_H$ (400 MHz, CDCl$_3$) 7.34 (3H, m), 7.23 (1H, t), 7.19 (1H, s), 7.02 (2H, m), 6.60 (1H, d), 5.70 (1H, s), 4.56 (2H, s), 3.70 (2H, s), 3.56 (4H, m), 3.29 (2H, dt) and 2.83 (1H, s); LCMS $R_t$=3.97 min, m/z (ES+) 441 (M+Na).

Using the above procedures the following additional compounds were also prepared:

Example [02]

N-[2-(2-Hydroxyethoxy)-ethyl]-C-[2-(2,4,6-trichlorophenylamino)-phenyl]-methanesulfonamide $\delta_H$ (400 MHz, CDCl$_3$) 7.38 (2H, s), 7.34 (1H, d), 7.24 (1H, t), 7.16 (1H, s), 7.06 (1H, t), 6.61 (1H, d), 5.01 (1H, t), 4.56 (2H, s), 3.75 (2H, q), 3.61 (4H, m), 3.32 (2H, q) and 2.02 (1H, t); LCMS $R_t$=1.90 min, m/z (ES+) 455 (M+H).

Example [03]

1-[2-(2,6-Dichloro-4-trifluoromethyl-phenylamino)-phenyl]-N-{2-(2-hydroxyethoxy)-ethyl]-methanesulfonamide $\delta_H$ (400 MHz, CDCl$_3$) 7.60 (2H, s), 7.49 (1H, s), 7.35 (1H, d), 7.28 (1H, t), 7.13 (1H, t), 6.70 (1H, d), 5.06 (1H, t), 4.56

(2H, s), 3.75 (2H, q), 3.61 (4H, m), 3.32 (2H, q) and 2.03 (1H, t); LCMS $R_t$=2.00 min, m/z (ES+) 487 (M+H).

Example [04]

1-[2-(2,6-Dichloro-3-methyl-phenylamino)-phenyl]-N-{2-(2-hydroxyethoxy)-ethyl}-methanesulfonamide $\delta_H$(400 MHz, CDCl$_3$) 7.34 (1H, d), 7.24 (2H, m), 7.12 (1H, s), 7.03 (1H, t), 6.98 (1H, d), 6.60 (1H, d), 5.13 (1H, t), 4.58 (2H, s), 3.74 (2H, q), 3.60 (4H, m), 3.33 (2H, q), 2.40 (3H, s) and 2.15 (1H, t); LCMS $R_t$=1.57 min, m/z (ES+) 433 (M+H).

Example [05]

N-(2-Hydroxyethyl)-C-[3-(2,4,6-trichlorophenylamino)-phenyl]-methane sulfonamide (I)

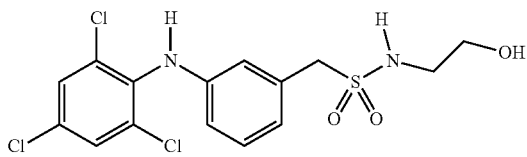 [SMILES: O=S(=O)(Cc1cccc(Nc2c(Cl)cc(Cl)cc2Cl)c1)NCCO]

C-(3-Aminophenyl)-N-(2-hydroxyethyl)-methanesulfonamide (V)

To a stirred solution of 2-(tert-butyldiphenyl-silanyloxy)-ethylamine (0.76 g, 2.54 mmol) in dichloromethane (15 ml) and pyridine (0.21 ml, 2.54 mmol) at room temperature was added 3-nitro-alpha-toluenesulfonyl chloride (0.50 g, 2.12 mmol) in one portion and the reaction stirred overnight. The reaction was diluted with dichloromethane (35 ml), washed with aqueous copper sulfate and brine, dried over sodium sulfate and concentrated to give a crude product. The crude N-[2-(tert-butyldiphenyl-silanyloxy)-ethyl]-C-(3-nitrophenyl)-methanesulfonamide (theoretical 1.06 g, 2.13 mmol) was dissolved in methanol (30 ml) and placed under an atmosphere of nitrogen prior to the addition of 10% Pd/C (10 Wt %, 100 mg) in one portion. The reaction mixture was evacuated, placed under an atmosphere of hydrogen (1 bar) and stirred vigorously overnight. The reaction was filtered through celite and the filtrate was concentrated in vacuo to afford the crude reduced product. The crude C-(3-aminophenyl)-N-[2-(tert-butyldiphenylsilanyloxy)-ethyl]methanesulfonamide obtained above (theoretical 0.996 g) was dissolved in tetrahydrofuran (20 ml) and a 1M solution of tetrabutlyammonium fluoride in tetrahydrofuran (2.34 ml, 2.34 mmol) was added in one portion. The reaction was stirred at room temperature for 2 h then diluted with ethyl acetate (30 ml) and brine (30 ml), the organic layer was dried over sodium sulfate, filtered and concentrated in vacuo. The crude mixture was purified by column chromatography using dichloromethane:methanol as eluent to give the named product (0.411 g, 84% over 3 steps); $R_f$(DCM:MeOH 95:5) 0.06; LCMS $R_t$=0.83 min, m/z (ES–) 229 (M–H).

N-(2-Hydroxyethyl)-C-[3-(2,4,6-trichlorophenylamino)-phenyl]-methane sulfonamide (I)

To a stirred solution of C-(3-Aminophenyl)-N-(2-hydroxyethyl)-methanesulfonamide (200 mg, 0.87 mmol), 1,3,5-trichloro-2-bromobenzene (283 mg, 1.09 mmol), K$_2$CO$_3$ (300 mg, 2.17 mmol) and XantPhos (50 mg, 0.09 mmol) in 1,4-dioxane (2 ml) under nitrogen in a microwave tube was added Pd$_2$dba$_3$ (40 mg, 0.04 mmol) in one portion and the tube sealed. The reaction was heated with stirring in a microwave at 150° C. for 60 minutes. The reaction was cooled before filtering through celite. The crude reaction mixture was part-purified by column chromatography eluting with ethyl acetate:hexane and the concentrated fractions further purified by preparative chromatography under acidic conditions to afford the named product (17.8 mg, 5%); $\delta_H$ (400 MHz, DMSO) 8.00 (1H, s), 7.76 (2H, s), 7.12 (1H, t), 6.99 (1H, t), 6.76 (1H, d), 6.62 (1H, s), 6.48 (1H, d), 4.69 (1H, brs), 4.21 (2H, s), 3.39 (2H, m) and 2.93 (2H, q); LCMS $R_t$=3.83 min, m/z (ES–) 409 (M–H).

Using the above procedures the following additional compounds were also prepared:

Example [06]

N-[2-(2-Hydroxyethoxy)-ethyl]-C-[3-(2,4,6-trichlorophenylamino)-phenyl]-methane sulfonamide $\delta_H$ (400 MHz, DMSO) 8.00 (1H, s), 7.76 (2H, s), 7.13 (2H, m), 6.76 (1H, d), 6.62 (1H, s), 6.49 (1H, d), 4.59 (1H, t), 4.22 (2H, s), 3.49 (2H, m), 3.40 (4H, m) and 3.03 (2H, q); LCMS $R_t$=3.86 min, m/z (ES+) 453 (M+H).

Example [07]

1-[3-(2,6-Dichloro-4-trifluoromethylphenylamino)-phenyl]-N-[2-(2-hydroxyethoxy)-ethyl]-methane sulfonamide $\delta_H$ (400 MHz, DMSO) 8.31 (1H, s), 7.96 (2H, s), 7.18 (1H, t), 7.10 (1H, t), 6.85 (1H, d), 6.72 (1H, s), 6.60 (1H, d), 4.59 (1H, t), 4.25 (2H, s), 3.50 (2H, m), 3.40 (4G, m) and 3.03 (2H, q); LCMS $R_t$=7.65 min, m/z (ES–) 485 (M–H).

Example [08]

N-(2-Hydroxyethyl)-2-(2,4,6-trichlorophenylamino)-benzenesulfonamide (I)

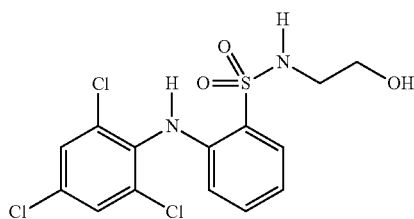 [SMILES: O=S(=O)(NCCO)c1ccccc1Nc1c(Cl)cc(Cl)cc1Cl]

N-(2-Hydroxyethyl)-2-nitrobenzene sulfonamide (IV)

To a stirred solution of 2-nitrobenzenesulfonyl chloride (5.00 g, 22.56 mmol) in dichloromethane (100 ml) and pyridine (1.91 ml, 23.69 mmol) at room temperature was added ethanolamine (1.38 g, 22.56 mmol) in one portion and the reaction stirred overnight. The reaction was diluted with dichloromethane (35 ml), washed with aqueous copper sulfate and brine, dried over sodium sulfate and concentrated onto silica. The reaction was purified by column chromatography using hexane:ethyl acetate as eluent to give the named product (1.25 g, 23%); R$_f$ (ethyl acetate:hexane 1:1) 0.08, LCMS R$_t$=2.25 min, m/z (ES+) 247 (M+H).

2-Amino-N-(2-hydroxyethyl)-benzene sulfonamide (V)

N-(2-Hydroxyethyl)-2-nitrobenzene sulfonamide (1.25 g, 5.08 mmol) was dissolved in methanol (50 ml) and placed under an atmosphere of nitrogen prior to the addition of 10% Pd/C (10 Wt %, 125 mg) in one portion. The reaction was evacuated, placed under an atmosphere of hydrogen (1 bar) and stirred vigorously overnight. The reaction was filtered through celite and the filtrate was concentrated in vacuo to afford the named product (0.88 g, 80%); LCMS R$_t$=2.05 min, m/z (ES+) 217 (M+H).

N-(2-Hydroxyethyl)-2-(2,4,6-trichlorophenylamino)-benzenesulfonamide (I)

To a stirred solution of 2-Amino-N-(2-hydroxyethyl)-benzene sulfonamide (160 mg, 0.74 mmol), 1,3,5-trichloro-2-bromobenzene (241 mg, 0.93 mmol), K$_2$CO$_3$ (256 mg, 1.85 mmol) and xantphos (43 mg, 0.074 mmol) in acetonitrile (2 ml) under nitrogen in a microwave tube was added Pd$_2$dba$_3$ (34 mg, 0.037 mmol) in one portion and the tube sealed. The reaction was heated with stirring in a microwave at 160° C. for 120 minutes. The reaction was cooled before filtering through celite. The crude reaction mixture was part-purified by column chromatography eluting with ethyl acetate:hexane and the concentrated fractions further purified by preparative chromatography under acidic conditions to afford the named product (49.0 mg, 17%); δ$_H$ (400 MHz, DMSO) 7.83 (3H, m), 7.75+7.45 (1H, d), 7.59+7.10 (1H, s), 7.55+7.38 (1H, t), 7.16+6.95 (1H, t), 7.10+6.40 (1H, d), 4.73 (1H, m), 3.35 (2H, m) and 2.83 (2H, m); LCMS R$_t$=7.92 min, m/z (ES+) 397 (M+H).

Using the above procedures the following additional compounds were also prepared:

Example [09]

N-(2-Hydroxyethyl)-2-(2,6-dichlorophenylamino)-benzenesulfonamide

δ$_H$ (400 MHz, DMSO) 7.87 (1H, s), 7.73 (1H, d), 7.63 (3H, m), 6.95 (1H, t), 6.35 (1H, d), 4.75 (1H, m), 3.40 (1H, t), 3.35 (2H, brs) and 2.84 (2H, t); LCMS R$_t$=6.99 min, m/z (ES+) 361 (M+H).

Example [10]

2-(2,6-Dichloro-4-trifluoromethylphenylamino)-N-(2-hydroxyethyl)-benzenesulfonamide δ$_H$ (400 MHz, DMSO) 8.06 (2H, s), 7.91 (1H, t), 7.78 (2H, m), 7.44 (1H, t), 7.05 (1H, t), 6.56 (1H, d), 4.72 (1H, t), 3.40 (1H, q), and 2.83 (2H, q); LCMS R$_t$=8.24 min, m/z (ES+) 429 (M+H).

Example [11]

2-(2,6-Dichloro-3-methylphenylamino)-N-(2-hydroxyethyl)-benzenesulfonamide

δ$_H$ (400 MHz, DMSO) 7.84 (1H, brt), 7.73 (1H, d), 7.62 (1H, s), 7.52 (1H, d), 7.36 (2H, m), 6.94 (1H, t), 6.32 (1H, d), 4.72 (1H, t), 3.40 (1H, q), 2.86 (2H, q) and 2.39 (3H, s); LCMS R$_t$=7.55 min, m/z (ES+) 375 (M+H).

Example [12]

2-(2,6-Dichloro-4-trifluoromethylphenylamino)-N-[2-(2-hydroxyethoxy)-ethyl]-benzenesulfonamide δ$_H$ (400 MHz, DMSO) 8.06 (2H, s), 7.99 (1H, brs), 7.78 (2H, brd), 7.42 (1H, t), 7.05 (1H, t), 6.55 (1H, d), 4.58 (1H, brs), 3.43 (4H, m), 3.35 (2H, q) and 2.93 (2H, q); R$_t$=8.31, m/z (ES+) 473 (M+H).

Example [13]

2-(2,6-Dichloro-3-methylphenylamino)-N-[2-(2-hydroxyethoxy)-ethyl]-benzenesulfonamide δ$_H$ (400 MHz, DMSO) 7.91 (1H, brs), 7.73 (1H, d), 7.63 (1H, s), 7.51 (1H, d), 7.38 (2H, m), 6.92 (1H, t), 6.30 (1H, d) 4.56 (1H, brs), 3.43 (4H, m), 3.35 (2H, m), 2.93 (2H, t) and 2.40 (3H, s); R$_t$=7.65, m/z (ES+) 419 (M+H).

Example [14]

2-(3,5-Dichlorophenylamino)-N-[2-(2-hydroxyethoxy)-ethyl]-benzenesulfonamide

δ$_H$ (400 MHz, DMSO) 7.99 (1H, brs), 7.82 (1H, d), 7.76 (1H, brs), 7.58 (1H, t), 7.45 (1H, d), 7.18 (1H, t), 7.10 (3H, m) 4.52 (1H, brs), 3.40 (2H, m), 3.30 (4H, m), and 2.95 (2H, t); R$_t$=7.95, m/z (ES+) 405 (M+H).

Example [15]

N-[2-(2-Hydroxyethoxy)-ethyl]-2-(2,4,6-trichlorophenylamino)-benzenesulfonamide

δ$_H$ (400 MHz, DMSO) 7.93 (1H, brs), 7.85 (2H, s), 7.74 (1H, d), 7.60 (1H, brs), 7.40 (1H, t), 7.10 (1H, d), 6.95 (1H, t), 6.40 (1H, d), 4.58 (1H, brs), 3.43 (4H, m), 3.38 (2H, m) and 2.96 (2H, t); R$_t$=8.03, m/z (ES+) 441 (M+H).+

Example [16]

N-(2-Hydroxyethyl)-3-(2,4,6-trichlorophenylamino)-benzenesulfonamide (I)

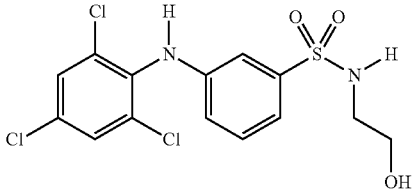 [SMILES: O=S(=O)(NCCO)c1cccc(Nc2c(Cl)cc(Cl)cc2Cl)c1]

2-Chloro-N-(2-hydroxyethyl)-5-nitro-benzene-sulfonamide (IV)

To a stirred solution of 2-(tert-butyldiphenylsilanyloxy) ethylamine (4.68 g, 15.63 mmol) in dichloromethane (50 ml) and pyridine (1.40 ml, 17.19 mmol) at room temperature was added 2-chloro-5-nitro-benzenesulfonylchloride (4.00 g, 15.63 mmol) in one portion and the reaction stirred overnight. The reaction was diluted with dichloromethane (35 ml), washed with aqueous copper sulfate and brine, dried over sodium sulfate and concentrated to give a crude product.

The crude N-[2-(tert-butyldiphenylsilanyloxy)-ethyl]-2-chloro-5-nitro-benzenesulfonamide obtained above (theoretical 8.09 g) was dissolved in tetrahydrofuran (50 ml) and a 1M solution of tetrabutlyammonium fluoride in tetrahydrofuran (17.2 ml, 17.2 mmol) was added in one portion. The reaction was stirred at room temperature for 2 h then diluted with ethyl acetate (30 ml) and brine (30 ml), the organic layer was dried over sodium sulfate, filtered and concentrated in vacuo. The reaction was purified by column chromatography using hexane: ethyl acetate as eluent to afford the named product (3.44 g, 79% over 2 steps); $R_f$ (ethyl acetate:hexane 1:1) 0.11, LCMS $R_t$=2.85 min, m/z (ES−) 279 (M−H).

3-Amino-N-(2-hydroxyethyl)-benzenesulfonamide (V)

2-Chloro-N-(2-hydroxyethyl)-5-nitro-benzenesulfonamide (1.00 g, 3.57 mmol) was dissolved in methanol (35 ml) and placed under an atmosphere of nitrogen prior to the addition of 10% Pd/C (10 Wt %, 100 mg) in one portion. The reaction was evacuated, placed under an atmosphere of hydrogen (1 bar) and stirred vigorously overnight. The reaction was filtered through celite and the filtrate was concentrated in vacuo to afford the named product (0.77 g, 100%); LCMS $R_t$=1.44 min, m/z (ES+) 217 (M+H).

N-(2-Hydroxyethyl)-3-(2,4,6-trichlorophenylamino)-benzenesulfonamide (I)

To a stirred solution of 3-Amino-N-(2-hydroxyethyl)-benzene sulfonamide (200 mg, 0.93 mmol), 1,3,5-trichloro-2-bromobenzene (301 mg, 1.16 mmol), $K_2CO_3$ (319 mg, 2.31 mmol) and XantPhos (54 mg, 0.093 mmol) in acetonitrile (2 ml) under nitrogen in a microwave tube was added $Pd_2dba_3$ (43 mg, 0.047 mmol) in one portion and the tube sealed. The reaction was heated with stirring in a microwave at 150° C. for 45 minutes. The reaction was cooled before filtering through celite. The crude reaction mixture was part-purified by column chromatography eluting with ethyl acetate:hexane and the concentrated fractions further purified by preparative chromatography under acidic conditions to afford the named product (96.3 mg, 26%); $\delta_H$ (400 MHz, DMSO) 8.45 (1H, s), 7.82 (2H, s), 7.54 (1H, t), 7.33 (1H, t), 7.13 (1H, d), 6.93 (1H, s), 6.76 (1H, d), 4.70 (1H, brs), 3.35 (2H, m) and 2.75 (2H, q); LCMS $R_t$=3.79 min, m/z (ES−) 392 (M−H)

Using the above procedures the following additional compounds were also prepared:

Example [17]

3-(2,6-Dichloro-4-trifluoromethylphenylamino)-N-(2-hydroxyethyl)-benzenesulfonamide $\delta_H$ (400 MHz, DMSO) 8.72 (1H, brs), 8.02 (2H, s), 7.59 (1H, brs), 7.39 (1H, t), 7.20 (1H, d), 7.03 (1H, s), 6.88 (1H, d), 4.70 (1H, brt), 3.36 (2H, m) and 2.76 (2H, t); LCMS $R_t$=7.45 min, m/z (ES+) 429 (M+H).

Example [18]

2-Chloro-N-(2-hydroxyethyl)-5-(2,4,6-trichlorophenylamino)benzensulfonamide $\delta_H$ (400 MHz, DMSO) 7.99 (1H, s), 7.89 (2H, s), 7.69 (1H, brt), 7.60 (1H, d), 7.13 (1H, d), 6.50 (1H, s), 4.68 (1H, t), 3.30 (2H, q) and 2.70 (2H, q); LCMS $R_t$=7.59 min, m/z (ES−) 429 (M−H).

Example [19]

2-Chloro-5-(2,6-dichloro-4-trifluoromethyl-phenylamino)-N-(2-hydroxyethyl)-benzenesulfonamide $\delta_H$ (400 MHz, DMSO) 8.19 (1H, s), 8.11 (2H, s), 7.69 (1H, brt), 7.64 (1H, d), 7.22 (1H, d), 6.65 (1H, s), 4.68 (1H, t), 3.31 (2H, q) and 2.70 (2H, q); LCMS $R_t$=7.97 min, m/z (ES−) 463 (M−H).

Test Examples

Summary

The objective of this study was to examine the in vitro effects of the Example compounds on the KCNQ2/KCNQ3 potassium channel current expressed in mammalian cells using the PatchXpress 7000A (Molecular Devices), an automatic parallel patch-clamp system. The test compounds were evaluated at 30 or 10 μM (n≦2). The duration of exposure to the test compound was 5 minutes. The compounds were found to produce a concentration-dependent enhancement of the current. Table 1 shows the individual results for a sample of the compounds. The results for a positive control, flupirtine (Table 2) applied to naïve cells in the same study confirm the sensitivity of the test system to detect KCNQ2/KCNQ3 current enhancement.

Methods

Cell Treatments

All experiments were performed at ambient temperature. Each cell acted as its own control.

Test Article Treatment Groups

A 30 μM or 10 μM concentration of test compound was applied via disposable polyethylene micropipette tips to naïve cells. Each solution exchange, performed in quadruplicate, consisted of aspiration and replacement of 45 μL of the total 50 μL volume of the extracellular well of the Sea/chip$_{16}$.

Positive Control Treatment Groups

Vehicle was applied to naïve cells (n≦2), for a 5 minute exposure interval.

Each solution exchange, performed in quadruplicate, consisted of aspiration and replacement of 45 μL of the total 50 μL volume of the extracellular well of the Sea/chip$_{16}$. After vehicle application, the positive control was applied in the same manner, to verify sensitivity of the assay.

Automated Patch-Clamp Procedures

In preparation for a recording session, intracellular solution was loaded into the intracellular compartments of the Sea/chip$_{16}$ planar electrode. Cell suspension was pipetted into the extracellular compartments of the Sea/chip$_{16}$ planar electrode. After establishment of the whole-cell configuration, membrane currents were recorded using dual-channel patch-clamp amplifiers in the PatchXpress® system. Before digitization, the current records were low-pass filtered at one-fifth of the sampling frequency.

Data Analysis

Data acquisition and analysis were performed using the pCLAMP suite of programs (Axon Instruments, Union City, Calif.). The steady-state current before and after test article application was used to calculate the percentage current enhancement at each concentration. The results obtained from different cells were averaged and presented as mean±s.e.m (see Tables 1 and 2).

TABLE 1

| Test Article ID | Concentration (μM) | n | Mean % Enhancement of KCNQ2/KCNQ3 |
|---|---|---|---|
| Example 1 | 30 | 2 | 32.4 ± 18 |
| Example 8 | 30 | 3 | 41.2 ± 9 |
| Example 9 | 30 | 3 | 56.8 ± 9 |
| Example 16 | 30 | 3 | 87.4 ± 14 |
| Example 18 | 10 | 3 | 18.6 ± 4 |

Positive Control

TABLE 2

| Test Article ID | Concentration (μM) | n | Mean % Enhancement of KCNQ2/KCNQ3 |
|---|---|---|---|
| Flupirtine | 10 | 11 | 127 ± 16% |

It can be seen from the results in Table 1 that the example compounds of the present application showed robust enhancement of the KCNQ2/KCNQ3 potassium channel current.

The invention claimed is:

1. A compound of formula (I) or a pharmacologically acceptable salt or pro-drug thereof wherein:

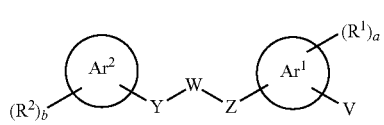

$Ar^1$ and $Ar^2$ are each phenyl; are the same or different and each is an aryl group or a heteroaryl group;
a is an integer of from 0 to 5;
$R^1$ is selected from the group consisting of alkyl groups, halogen atoms, haloalkyl groups, alkoxy groups, alkoxycarbonyl groups, carboxyl groups, hydroxyl groups, amino groups, monalkylamino groups, dialkylamino groups, acylamino groups, alkoxycarbonylamino groups, alkylsulphonyl groups, alkylsulphonylamino groups and cyano groups and, where a is greater than 1, each substituent $R^1$ may be the same or different;
b is an integer of from 0 to 5;
$R^2$ is selected from the group consisting of alkyl groups, halogen atoms, haloalkyl groups, alkoxy groups, alkoxycarbonyl groups, carboxyl groups, hydroxyl groups, amino groups, monalkylamino groups, dialkylamino groups, nitro groups, acylamino groups, alkoxycarbonylamino groups, alkylsulphonyl groups, alkylsulphonylamino groups and cyano groups and where b is greater than 1, each substituent $R^2$ may be the same or different;
V is selected from the group consisting of $(CR^{3a}R^{3b})_p SO_2N(R^3b)X$;
W is $NR^{4a}$;
X is a substituent selected from the group consisting of hydroxyalkyl groups, and polyalkylene glycol residues;
Y and Z are each a group of formula $(CR^{5a}R^{5b})_{n1}$, wherein each n1 is 0; and
p is an integer of from 0 to 2,
and wherein V is substituting said $Ar^1$ at an ortho position with respect to said Z or said W.

2. A compound according to claim 1 or a pharmacologically acceptable salt or pro-drug thereof, wherein a is an integer of from 0 to 3.

3. A compound according to claim 1 or a pharmacologically acceptable salt or pro-drug thereof, wherein $R^1$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent $R^1$ may be the same or different.

4. A compound according to claim 1 or a pharmacologically acceptable salt or pro-drug thereof, wherein b is an integer of from 0 to 4.

5. A compound according to claim 1 or a pharmacologically acceptable salt or pro-drug thereof, wherein $R^2$ is selected from the group consisting of alkyl groups having from 1 to 3 carbon atoms, halogen atoms, haloalkyl groups having from 1 to 3 carbon atoms, alkoxy groups having from 1 to 3 carbon atoms, carboxyl groups, amino groups, hydroxyl groups and cyano groups.

6. A compound according to claim 1 or a pharmacologically acceptable salt or pro-drug thereof, wherein $R^{4a}$ is selected from the group consisting of hydrogen atoms, alkyl groups having from 1 to 3 carbon atoms and phenyl groups.

7. A compound according to claim 1 or a pharmacologically acceptable salt or pro-drug thereof, wherein V is selected from the group consisting of $(CR^{3a}R^{3b})_p SO_2N(R^{3b})X$, wherein p is an integer of from 0 to 2, $R^{3a}$ and $R^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms, and X is a substituent selected from the group consisting of hydroxyalkyl groups having from 1 to 6 carbon atoms, and polyalkylene glycol residues of general formula HO—[(CR($CR^{6a}R^{6b}$)$_{c1}$—O—($CR^{6c}R^{6d}$)$_{c2}$]$_{c3}$— wherein c1 and c2 are the same or different and each is an integer of from 0 to 4, c3 is an integer of from 1 to 20 and $R^{6a}$, $R^{6b}$, $R^{6c}$ and $R^{6d}$ may be the same or different from each other and each is a hydrogen atom or an alkyl group having from 1 to 6 carbon atoms.

8. A compound according to claim 1 or a pharmacologically acceptable salt or pro-drug thereof, wherein V is a group of formula of $(CR^{3a}R^{3b})_p SO_2N(R^{3b})X$, wherein p is an integer of 0 or 1, $R^{3a}$ and $R^{3b}$ are the same or different and each is selected from the group consisting of hydrogen atoms and alkyl groups having from 1 to 4 carbon atoms, and X is a substituent selected from the group consisting of hydroxyalkyl groups having from 1 to 4 carbon atoms and polyalkylene glycol residues of general formula HO—[($CR^{6a}R^{6b}$)$_{c1}$—O—($CR^{6c}R^{6d}$)$_{c2}$]$_{c3}$— wherein c1 and c2 are the same or different and each is an integer of from 1 to 3, c3 is an integer of from 1 to 10 and $R^{6a}, R^{6b}, R^{6c}, R^{6d}$ may be the same or different and each is a hydrogen atom or an alkyl group having from 1 to 4 carbon atoms.

9. A compound according to claim 1 or a pharmacologically acceptable salt or pro-drug thereof, wherein V is a group of formula of $(CR^{3a}R^{3b})_p SO_2N(R^{3b})X$, wherein p is an integer of 0 or 1, each of $R^{3a}$ and $R^{3b}$ is a hydrogen atom, and X is a hydroxylalkyl group having from 1 to 4 carbon atoms or a polyalkylene glycol residue of general formula HO—$[CR^{6a}R^{6b})_{c1}$—O—$(CR^{6c}R^{6d})_{c2}]_{c3}$— wherein c1 and c2 are the same or different and each is 1 or 2, c3 is an integer of from 1 to 6 and each of $R^{6a}, R^{6b}, R^{6c}$ and $R^{6d}$ is a hydrogen atom.

10. A compound according to claim 1 or a pharmacologically acceptable salt or pro-drug thereof, wherein:

$Ar^1$ and $Ar^2$ are each phenyl;

a is an integer of from 0 to 3;

$R^1$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where a is greater than 1, each substituent $R^1$ may be the same or different;

b is an integer of from 0 to 4;

$R^2$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where b is greater than 1, each substituent $R^2$ may be the same or different;

W is $NR^{4a}$, wherein $R^{4a}$ is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms;

Y and Z are each a group of formula $(CR^{5a}R^{5b})_{n1}$, wherein each n1 is 0; and V is selected from the group consisting of $(CR^{3a}R^{3b})_p SO_2N(R^{3b})X$ and, wherein p is an integer of from 0 to 2, $R^{3a}$ and $R^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms which may optionally be substituted with at least one substituent selected from alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, carbonyl groups, hydroxyl groups and cyano groups, and 5- to 7-membered aromatic heterocyclic groups containing from 1 to 3 sulfur atoms, oxygen atoms and/or nitrogen atoms, and X is a substituent selected from the group consisting of hydroxyalkyl groups having from 1 to 6 carbon atoms, and polyalkylene glycol residues of general formula HO-$[(CR^{6a}R^{6b})_{c1}$—O—$(CR^{6c}R^{6d})_{c2}]_{c3}$— wherein c1 and c2 are the same or different and each is an integer of from 0 to 4, c3 is an integer of from 1 to 20 and $R^{6a}, R^{6b}, R^{6c}$ and $R^{6d}$ may be the same or different from each other and each is a hydrogen atom or an alkyl group having from 1 to 6 carbon atoms.

11. A compound according to claim 1 or a pharmacologically acceptable salt or pro-drug thereof, wherein:

$Ar^1$ and $Ar^2$ are each phenyl;

a is 0 or 1;

$R^1$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent $R^1$ may be the same or different;

b is an integer of from 0 to 3;

$R^2$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, nitro groups, acylamino groups having from 1 to 4 carbon atoms, alkylsulphonyl groups having from 1 to 4 carbon atoms, alkylsulphonylamino groups having from 1 to 4 carbon atoms and cyano groups and, where b is greater than 1, each substituent $R^2$ may be the same or different;

W is $NR^{4a}$, wherein $R^{4a}$ is selected from the group consisting of hydrogen atoms, alkyl groups having from 1 to 4 carbon atoms, aryl groups having from 6 to 10 carbon atoms and 5- or 6-membered aromatic heterocyclic groups containing 1 or 2 sulfur atoms, oxygen atoms and/or nitrogen atoms;

Y and Z are each a group of formula $(CR^{5a}R^{5b})_{n1}$, wherein each n1 is 0; and V is a group of formula of $(CR^{3a}R^{3b})_p SO_2N(R^{3b})X$, wherein p is an integer of 0 or 1, $R^{3a}$ and $R^{3b}$ are the same or different and each is selected from the group consisting of hydrogen atoms and alkyl groups having from 1 to 4 carbon atoms, and X is a substituent selected from the group consisting of hydroxyalkyl groups having from 1 to 4 carbon atoms and polyalkylene glycol residues of general formula HO—[$(CR^{6a}R^{6b})_{c1}$—O—$(CR^{6c}R^{6d})_{c2}]_{c3}$— wherein c1 and c2 are the same or different and each is an integer of from 1 to 3, c3 is an integer of from 1 to 10 and $R^{6a}$, $R^{6b}$, $R^{bc}$ and $R^{6d}$ may be the same or different and each is a hydrogen atom or an alkyl group having from 1 to 4 carbon atoms.

12. A compound according to claim 1 or a pharmacologically acceptable salt or pro-drug thereof, wherein:

$Ar^1$ and $Ar^2$ are each phenyl;

a is 0 or 1;

$R^1$ is selected from the group consisting of alkyl groups having from 1 to 4 carbon atoms, halogen atoms, haloalkyl groups having from 1 to 4 carbon atoms, alkoxy groups having from 1 to 4 carbon atoms, carboxyl groups, hydroxyl groups, amino groups, monalkylamino groups wherein the alkyl group has from 1 to 4 carbon atoms, dialkylamino groups wherein the alkyl groups may be the same or different and each has from 1 to 4 carbon atoms, acylamino groups having from 1 to 4 carbon atoms, alkylsulphonyl groups having from 1 to 4 carbon atoms, alkylsulphonylamino groups having from 1 to 4 carbon atoms and cyano groups and, where a is greater than 1, each substituent $R^1$ may be the same or different;

b is 0 to 3;

$R^2$ is selected from the group consisting of alkyl groups having from 1 to 3 carbon atoms, halogen atoms, haloalkyl groups having from 1 to 3 carbon atoms, alkoxy groups having from 1 to 3 carbon atoms, carboxyl groups, amino groups, hydroxyl groups and cyano groups;

W is a group of formula $NR^{4a}$, wherein $R^{4a}$ is selected from the group consisting of hydrogen atoms, alkyl groups having from 1 to 3 carbon atoms and phenyl groups;

Y and Z are each a group of formula $(CR^{5a}R^{5b})_{n1}$ wherein each n1 is 0; and V is a group of formula of $(CR^{3a}R^{3b})_p SO_2N(R^{3b})X$, wherein p is an integer of 0 or 1, each of $R^{3a}$ and $R^{3b}$ is a hydrogen atom, and X is a hydroxyalkyl group having from 1 to 4 carbon atoms or a polyalkylene glycol residue of general formula HO—[$(CR^{6a}R^{6b})_{c1}$—O—$(CR^{6c}R^{6d})_{c2}]_{c3}$— wherein c1 and c2 are the same or different and is 1 or 2, c3 is an integer of from 1 to 6 and each of $R^{6a}$, $R^{6b}$, $R^{6c}$ and $R^{6d}$ is a hydrogen atom.

13. A compound according to claim 1 or a pharmacologically acceptable salt or pro-drug thereof, wherein:

$Ar^1$ and $Ar^2$ are each phenyl;

a is an integer of from 0 to 3;

$R^1$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where a is greater than 1, each substituent $R^1$ may be the same or different;

b is an integer of from 0 to 4;

$R^2$ is selected from the group consisting of alkyl groups having from 1 to 6 carbon atoms, halogen atoms, haloalkyl groups having from 1 to 6 carbon atoms, alkoxy groups having from 1 to 6 carbon atoms, alkoxycarbonyl groups wherein the alkoxy group has from 1 to 6 carbon atoms, carboxyl groups, hydroxyl groups, amino groups, monalkylamino groups wherein the alkyl group has from 1 to 6 carbon atoms, dialkylamino groups wherein the alkyl groups may be the same or different and each has from 1 to 6 carbon atoms, nitro groups, acylamino groups having from 1 to 6 carbon atoms, alkoxycarbonylamino groups wherein the alkoxy group has from 1 to 6 carbon atoms, alkylsulphonyl groups having from 1 to 6 carbon atoms, alkylsulphonylamino groups having from 1 to 6 carbon atoms and cyano groups and, where b is greater than 1, each substituent $R^2$ may be the same or different;

W is $NR^{4a}$, wherein $R^{4a}$ is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms; and V is selected from the group consisting of $(CR^{3a}R^{3b})_p SO_2N(R^{3b})X$ wherein p is an integer of from 0 to 2, $R^{3a}$ and $R^{3b}$ are the same or different and each is selected from the group consisting of hydrogen atoms, alkyl groups having from 1 to 6 carbon atoms, cycloalkyl groups having from 3 to 7 carbon atoms, aryl groups having from 5 to 14 carbon atoms and 5- to 7-membered aromatic heterocyclic groups containing from 1 to 3 sulfur atoms, oxygen atoms and/or nitrogen atoms, and X is a substituent selected from the group consisting of hydroxyalkyl groups having from 1 to 6 carbon atoms, and polyalkylene glycol residues of general formula HO—[$(CR^{6a}R^{6c})_{c1}$—O—$(CR^{6c}R^{6d})_{c2}]_{c3}$— wherein c1 and c2 are the same or different and each is an integer of from 0 to 4, c3 is an integer of from 1 to 20 and $R^{6a}$, $R^{6b}$, $R^{6c}$ and $R^{6d}$ may be the same or different from each other and each is a hydrogen atom or an alkyl group having from 1 to 6 carbon atoms.

14. A compound selected from the group consisting of:
1-[2-(2,6-Dichlorophenylamino)phenyl]-N-[2-(2-hydroxyethoxy)ethyl]-methanesulfonamide,
N-[2-(2-hydroxyethoxy)ethyl]-C-[2-(2,4,6-trichlorophenylamino)phenyl]-methanesulfonamide,
1-[2-(2,6-dichloro-4-trifluoromethylphenylamino)phenyl]-N-{2-(2-hydroxyethoxy)ethyl]methanesulfonamide,
1-[2-(2,6-dichloro-3-methylphenylamino)phenyl]-N-{2-(2-hydroxyethoxy)-ethyl]methanesulfonamide,
N-(2-hydroxyethyl)-1-[3-(2,4,6-trichlorophenylamino) phenyl]methane sulphonamide,
N-(2-hydroxyethyl)-2-(2,4,6-trichlorophenylamino)benzenesulfonamide,
N-(2-hydroxyethyl)-2-(2,6-dichlorophenylamino)benzene sulfonamide,
2-(2,6-dichloro-4-trifluoromethylphenylamino)-N-(2-hydroxyethyl)-benzenesulfonamide,
2-(2,6-dichloro-3-methylphenylamino)-N-(2-hydroxyethyl)-benzenesulfonamide,
2-(2,6-dichloro-4-trifluoromethylphenylamino)-N-[2-(2-hydroxyethoxy)ethyl]-benzenesulfonamide,
2-(2,6-dichloro-3-methylphenylamino)-N-[2-(2-hydroxyethoxy)ethyl]-benzenesulfonamide, 2-(3,5-dichlorophenylamino)-N-[2-(2-hydroxyethoxy)ethyl]-benzenesulfonamide, and N-[2-(2-hydroxyethoxy)ethyl]-2-(2,4,6-trichlorophenylamino)-benzenesulfonamide, or a pharmacologically acceptable salt or pro-drug thereof.

15. A pharmaceutical composition comprising a pharmacologically acceptable diluent or carrier and an active ingredient, wherein said active ingredient is a compound according to claim 1 or a pharmacologically acceptable salt or pro-drug thereof as an active ingredient thereof.

16. A method for modulating voltage-dependent potassium channels KCNQ2, KCNQ3 or KCNQ2/3 with a compound according to claim 1 or a pharmacologically acceptable salt or pro-drug thereof.

* * * * *